United States Patent
Bolton et al.

(10) Patent No.: US 11,442,006 B2
(45) Date of Patent: Sep. 13, 2022

(54) METHOD AND SYSTEM FOR DETECTING MOISTURE LEVELS IN WOOD PRODUCTS USING NEAR INFRARED IMAGING AND MACHINE LEARNING

(71) Applicant: Boise Cascade Company, Boise, ID (US)

(72) Inventors: David Bolton, Lena, LA (US); Jude Richard Peek, Pineville, LA (US); Curtis Fennell, Boyce, LA (US)

(73) Assignee: Boise Cascade Company, Boise, ID (US)

( * ) Notice: Subject to any disclaimer, the term of this patent is extended or adjusted under 35 U.S.C. 154(b) by 382 days.

(21) Appl. No.: 16/687,342

(22) Filed: Nov. 18, 2019

(65) Prior Publication Data

US 2020/0173915 A1 Jun. 4, 2020

Related U.S. Application Data

(60) Provisional application No. 62/774,029, filed on Nov. 30, 2018.

(51) Int. Cl.
*G01J 5/02* (2022.01)
*G01N 21/3559* (2014.01)
(Continued)

(52) U.S. Cl.
CPC ......... *G01N 21/3559* (2013.01); *F26B 25/22* (2013.01); *G01N 21/359* (2013.01);
(Continued)

(58) Field of Classification Search
CPC .. G01N 21/3559; G01N 21/359; G01N 21/86; G01N 33/46; G01N 2021/1765;
(Continued)

(56) References Cited

U.S. PATENT DOCUMENTS 3,566,937 A 3/1971 Erickson
3,606,942 A 9/1971 Daniels
(Continued)

FOREIGN PATENT DOCUMENTS

CN 110948613 4/2020
JP 2014205306 10/2014
(Continued)

OTHER PUBLICATIONS

Conners et al., "Machine vision technology for the forest products industry," 1997, IEEE, Computer, vol. 30. No. 7, pp. 43-48. (Year: 1997).

(Continued)

*Primary Examiner* — Stephen P Coleman
(74) *Attorney, Agent, or Firm* — Hawley Troxell Ennis & Hawley LLP; Philip McKay

(57) ABSTRACT

Near InfraRed NIR technology, including NIR cameras and detectors, and machine learning methods and systems, including one or more Machine Learning (ML) based moisture level detection models, are used to accurately identify moisture content and the specific locations of the moisture on an entire surface of a veneer sheet or other wood product and provide moisture level prediction data for the veneer sheet or other wood product. Based on the moisture level prediction data for a given wood product, one or more actions are taken with respect to wood product to ensure the wood product is put to the most efficient, effective, and valuable use.

20 Claims, 22 Drawing Sheets
(7 of 22 Drawing Sheet(s) Filed in Color)

(51) Int. Cl.

| | | |
|---|---|---|
| G01N 21/359 | (2014.01) | |
| G01N 21/86 | (2006.01) | |
| G06T 7/00 | (2017.01) | |
| G06T 7/90 | (2017.01) | |
| F26B 25/22 | (2006.01) | |
| G01N 33/46 | (2006.01) | |
| H04N 5/33 | (2006.01) | |
| H04N 5/225 | (2006.01) | |
| H04N 5/247 | (2006.01) | |
| G01N 21/17 | (2006.01) | |

(52) U.S. Cl.
CPC ............. *G01N 21/86* (2013.01); *G01N 33/46* (2013.01); *G06T 7/001* (2013.01); *G06T 7/0004* (2013.01); *G06T 7/90* (2017.01); *H04N 5/2256* (2013.01); *H04N 5/247* (2013.01); *H04N 5/33* (2013.01); *F26B 2210/14* (2013.01); *G01N 2021/1765* (2013.01); *G01N 2021/8663* (2013.01); *G01N 2201/062* (2013.01); *G06T 2207/10048* (2013.01); *G06T 2207/20081* (2013.01); *G06T 2207/20084* (2013.01); *G06T 2207/20212* (2013.01); *G06T 2207/30161* (2013.01)

(58) Field of Classification Search
CPC ..... G01N 2021/8663; G01N 2201/062; G01N 2021/845; G01N 21/3563; G01N 21/8986; F26B 25/22; F26B 2210/14; F26B 3/30; F26B 15/18; G06T 7/0004; G06T 7/001; G06T 7/90; G06T 2207/10048; G06T 2207/20081; G06T 2207/20084; G06T 2207/20212; G06T 2207/30161; H04N 5/2256; H04N 5/247; H04N 5/33
USPC ....................................................... 250/339.1
See application file for complete search history.

(56) References Cited

U.S. PATENT DOCUMENTS

| | | | |
|---|---|---|---|
| 4,630,424 | A | 12/1986 | Eberle et al. |
| 4,641,480 | A | 2/1987 | Mort |
| 4,797,169 | A | 1/1989 | Aizawa et al. |
| 4,872,299 | A | 10/1989 | Troutner |
| 4,893,961 | A | 1/1990 | O'Sullivan et al. |
| 4,942,084 | A | 7/1990 | Prince |
| 4,967,534 | A | 11/1990 | Lines |
| 5,892,808 | A | 4/1999 | Goulding et al. |
| 5,960,104 | A | 9/1999 | Conners et al. |
| 6,495,833 | B1 | 12/2002 | Alfano et al. |
| 6,543,604 | B1 | 4/2003 | Pung et al. |
| 9,164,029 | B2 | 10/2015 | Tsuchikawa et al. |
| 10,260,232 | B1 | 4/2019 | Conboy |
| 10,825,164 | B1 | 11/2020 | Bolton et al. |
| 10,933,556 | B2 | 3/2021 | Bolton et al. |
| 10,933,557 | B2 | 3/2021 | Bolton et al. |
| 11,090,833 | B2 | 8/2021 | Bolton et al. |
| 11,200,663 | B1 | 12/2021 | Bolton et al. |
| 11,222,419 | B1 | 1/2022 | Bolton et al. |
| 2003/0042180 | A1 | 3/2003 | Kairi |
| 2004/0146615 | A1 | 7/2004 | McDonald et al. |
| 2004/0206676 | A1 | 10/2004 | Dai et al. |
| 2005/0098728 | A1 | 5/2005 | Alfano et al. |
| 2005/0161118 | A1 | 7/2005 | Carman et al. |
| 2007/0131862 | A1 | 6/2007 | Cowan et al. |
| 2007/0137323 | A1 | 6/2007 | Stanley et al. |
| 2007/0143066 | A1 | 6/2007 | Stanley et al. |
| 2007/0143075 | A1 | 6/2007 | Stanley et al. |
| 2007/0222100 | A1 | 9/2007 | Husted et al. |
| 2007/0246125 | A1 | 10/2007 | Latos |
| 2008/0243424 | A1 | 10/2008 | Jones et al. |
| 2009/0279773 | A1 | 11/2009 | Gan et al. |
| 2010/0141754 | A1 | 6/2010 | Hiraoka |
| 2012/0301601 | A1 | 11/2012 | Jewell et al. |
| 2013/0333805 | A1 | 12/2013 | Gagnon et al. |
| 2016/0040933 | A1 | 2/2016 | Stanish |
| 2016/0067879 | A1 | 3/2016 | Capps |
| 2016/0103115 | A1 | 4/2016 | Hamby |
| 2016/0123871 | A1 | 5/2016 | Kalwa et al. |
| 2017/0023489 | A1 | 1/2017 | Iizuka et al. |
| 2018/0059014 | A1 | 3/2018 | Ruback et al. |
| 2019/0168413 | A1 | 6/2019 | Conboy |
| 2020/0171695 | A1 | 6/2020 | Bolton et al. |
| 2020/0173914 | A1 | 6/2020 | Bolton et al. |
| 2020/0175670 | A1 | 6/2020 | Bolton et al. |
| 2020/0234427 | A1 | 7/2020 | Cui et al. |
| 2021/0319548 | A1 | 10/2021 | Bolton et al. |
| 2021/0327049 | A1 | 10/2021 | Bolton et al. |
| 2021/0398269 | A1 | 12/2021 | Bolton et al. |
| 2021/0398270 | A1 | 12/2021 | Bolton et al. |

FOREIGN PATENT DOCUMENTS

| | | |
|---|---|---|
| JP | 2014215233 | 11/2014 |
| JP | 2019-166657 | 10/2019 |
| KR | 10-2019-0070756 | 6/2019 |
| WO | WO 2016-201553 | 12/2016 |
| WO | WO 2020-153848 | 7/2020 |

OTHER PUBLICATIONS

Nieminen et al., "Laser transillumination imaging for determining wood defects and grain angle," 2013, Measurement Science and Technology, vol. 24, No. 125401, 7 pages. (Year 2013).

Tsuchikawa et al., "A review of recent application of near infrared spectroscopy to wood science and technology," 2015, Journal of Wood Science, vol. 61, pp. 213-220. (Year: 2015).

Colares et al., "Near infrared hyperspectral imaging and MCR-ALS applied for mapping chemical composition of the wood specie Swietenia Macrophylla King (Mahogany) at microscopic level," 2016, Microchemical Journal, vol. 124, pp. 356-363. (Year: 2016).

Cognex Vision Software, "GigE Vision Cameras User's Guide," Published 2011.

Cognex, "Vision Controller Installation Manual," 2014.

Cognex, "Vision Product Guide," 2018.

USNR Transverse High Grader information sheet, copyright 2019; retrieved May 23, 2019 from https://www.usnr.com/en/product/THGLM.

USNR Lineal High Grader information sheet, copyright 2019; retrieved May 23, 2019 from https://www.usnr.com/en/product/LHGLM.

USNR LHG E-Valuator Module, copyright 2019; retrieved May 23, 2019 from https://www.usnr.com/en/product/LHGEValuatorLM.

USNR Planer/Dry Mill Optimization information sheet, copyright 2019; retrieved May 23, 2019 from https://www.usnr.com/en/product/mktoptplanermilllm.

Mecano Advantages information sheet, copyright 2019; retrieved May 23, 2019 from http://www.raute.com/mecano-advantages.

Mecano Solutions information sheet, copyright 2019; retrieved May 23, 2019 from http://www.raute.com/mecano-solutions.

Mecano Products information sheet, copyright 2019; retrieved May 23, 2019 from http://www.raute.com/264.

Drying Lines information sheets, copyright 2019; retrieved May 23, 2019 from http://www.raute.com/mecano-drying-lines?redirect=http%3A%2F%2Fwww.raute.com%2Flvl%3Fp_p_id%3%26p_plifecycle%3D0%26p_p_state% . . .

Layup Lines information sheet, copyright 2019; retrieved May 23, 2019 from http://www.raute.com/mecano-layup-lines.

Veneer Handling Lines information sheet, copyright 2019; retrieved May 23, 2019 from http://www.raute.com/mecano-veneer-handling-lines.

Panel Handling Lines information sheet, copyright 2019; retrieved May 23, 2019 from http://www.raute.com/mecano-panel-handling-lines.

(56) References Cited

OTHER PUBLICATIONS

Peeling Lines information sheet, copyright 2019; retrieved May 23, 2019 from http://www.raute.com/268.
Smart Mill Concept information sheet, copyright 2019; retrieved May 23, 2019 from http://www.raute.com/smart-mill-concept.

METHOD AND SYSTEM FOR DETECTING MOISTURE LEVELS IN WOOD PRODUCTS USING NEAR INFRARED IMAGING AND MACHINE LEARNING

RELATED APPLICATIONS

This application claims the benefit of David Bolton, U.S. Provisional Patent Application No. 62/774,029, filed on Nov. 30, 2018, entitled "NEAR-INFRARED MOISTURE DETECTION IN WOOD PRODUCTS," which is hereby incorporated by reference in its entirety as if it were fully set forth herein.

This application is related to U.S. patent application Ser. No. 16/687,311, naming David Bolton as inventor, filed concurrently with the present application on Nov. 18, 2019, entitled "METHOD AND SYSTEM FOR DETECTING MOISTURE LEVELS IN WOOD PRODUCTS USING NEAR INFRARED IMAGING," which is hereby incorporated by reference in its entirety as if it were fully set forth herein. This application is also related to U.S. patent application Ser. No. 16/687,369, naming David Bolton as inventor, filed concurrently with the present application on Nov. 18, 2019, entitled "METHOD AND SYSTEM FOR MOISTURE GRADING WOOD PRODUCTS USING SUPERIMPOSED NEAR INFRARED AND VISUAL IMAGES," which is hereby incorporated by reference in its entirety as if it were fully set forth herein.

BACKGROUND

There are numerous classes and types of wood products for use in a virtually limitless list of applications. Wood product types include, but are not limited to: raw wood products such as logs, debarked blocks, green or dry veneer, and dimensional lumber; intermediate wood components, such as wood I-beam flanges and webs; and finished wood products such as laminated beams, plywood panels, Laminated Veneer Lumber (LVL), and wood beam/I-beam products.

One important metric that must be taken into account when producing and utilizing wood products is the moisture content of the wood product and distribution of the moisture throughout the wood product. This is critical because the presence of various levels of moisture can determine if the particular sample of wood product is of acceptable quality for a specific use. Consequently, only by ensuring that the moisture level in a wood product is within specifically defined limits can the wood product be most cost-effectively and efficiently used, thereby ensuring the most valuable use of these natural resources.

As one specific illustrative example, veneer is a primary component of numerous intermediate and finished wood products. However, like most wood products, veneer can have widely varying levels of moisture from sheet to sheet and even within the same sheet. Therefore, when working with veneer to produce intermediate or finished wood products, such as plywood or LVL, it is important to determine as accurately as possible the overall moisture content and distribution of moisture throughout a given sheet of veneer. While this is particularly critical in the case of veneer, it is also important for any wood product and especially for those wood products used as layers or that are composed of layers. This is because the presence of various levels of moisture in these wood products determines if the particular wood product under consideration will remain structurally sound during and after processing.

Veneer is typically created by peeling thin layers of wood from a parent log, or other lumber source, in a continuous manner. This process is similar to unrolling a bolt of cloth. The resulting relatively thin veneer layer or "ribbon" is then cut to specific veneer sheet dimensions. Typically, the resulting veneer sheets are then dried and stacked in layers and glued to each other under pressure and heat to produce a multilayer intermediate or finished wood product, such as LVL.

The use of veneer in this way allows wood products of various thickness and dimensions to be created without milling a board of the desired thickness or dimension from a single log or single piece of lumber. This, in turn, allows for much more efficient use of natural resources. Indeed, without the use of various layered wood technologies, such as veneer products, the forests of the planet would have been depleted long ago simply to meet the construction needs of the ever-increasing world population. However, the presence of excess moisture in veneer sheets can create serious problems. This is because, as noted above, the layers of veneer sheets, or any wood component used to produce a layered wood product, are glued together using heat and pressure. When the layers of veneer sheets, or other wood product, are stacked, moisture in the individual veneer layers can become trapped between these layers in moisture pockets. Then, when the stacked layers are subjected to pressure and heat, the moisture in the pockets becomes vaporized with no avenue of escape. Consequently, the vapor pressure can build to the point that pockets of trapped moisture create imperfections and bulges in the layered structure and/or the surface of the wood product. In some cases, the trapped vapor even causes cracks or structural blowouts in the layered wood product. This, of course, results in compromised structural integrity of the layered wood product and/or undesirable imperfections in the appearance of the layered wood product.

Therefore, there exists a long-standing technical problem of accurately determining the moisture level of wood products, and in particular, the moisture level of wood products, such as veneer sheets, that are to be used as components of layered wood products. In addition, any method or system used to detect moisture levels in wood products must also be effective and efficient enough to detect the moisture while not significantly slowing down the production process or otherwise adding to the cost of the end wood product.

Traditionally, the problem of detecting moisture levels in wood products such as veneer sheets has been addressed in one of two ways; using contact electrode moisture detection systems or using RF moisture detection systems.

FIG. 1A is an illustration of one example of a prior art traditional contact electrode system 100.

Using traditional contact electrode systems, such as traditional contact electrode system 100, a veneer sheet 103, or other wood product, is moved along a production conveyor belt or other conveyance system. At one or more points along the conveyor belt one or more high-voltage contact electrodes structures 101 are positioned in physical contact with a surface 105 of the veneer sheet 103, or other wood product.

FIG. 1B is an illustration of one example of a contact electrode structure 101 of a prior art traditional contact electrode system. As seen in FIG. 1B, in some cases, the contact electrodes structure 101 can take the form of metallic brushes whose electrode elements 102 are kept in contact with the surface 105 of the veneer sheet 103, or other wood product, as the veneer sheet 103, or other wood product, moves below the electrode elements 102.

Various sub-systems 107 have historically been utilized to maintain contact pressure between the surface 105 of the veneer sheet 103, or other wood product, and the contact electrode elements 102. Traditionally, these include springs or weight loading. As discussed below, this configuration can represent a problem since this physical contact can damage either the surface 105 of the veneer sheet 103, or other wood product, or damage the contact electrode structures 101, or both.

Using traditional contact electrode systems, the electrodes must remain in contact with the surface of the veneer sheet being analyzed, and at specific distances from each other. This causes several issues given that the veneer sheet or other wood product moving beneath the electrodes is often uneven and therefore can easily damage and/or displace the electrodes, damage the surface of the veneer or other wood product, or damage both. This often results in damaged product and the need to replace electrodes. In addition, this physical contact configuration and the resulting damaged components also results in inconsistent readings and data. Further, maintaining a constant pressure of the electrodes with the surface of the veneer or other wood product is also difficult given the typically uneven surfaces of the veneer layer or wood product.

FIG. 1C is a graphical representation of the placement and spacing of individual contact electrodes 101 using a typical traditional contact electrode system 100. As seen in FIG. 1C, contact electrodes 101 are spaced in rows 120 separated by row distances 121 and columns 130 separated by column distances 131. Consequently, each row 120 defines a sample channel, such as sample channels 1 through 8, in FIGS. 1C and 1D (discussed below) as the surface 105 of the veneer sheet 103, or other wood product, moves underneath contact electrodes 101 in direction 139.

FIG. 1D shows a typical sample sheet 140 generated using traditional contact electrode systems and the physical arrangement of FIG. 1C. Referring to FIGS. 1C and 1D, each sample channel 1 through 8 in FIG. 1D includes multiple sample areas 151. In the specific illustrative example of FIG. 1D each sample channel 1 through 8 includes 16 sample areas 151. Consequently, since there are 8 channels, there are 128 sample areas in this example of a typical configuration. In the specific illustrative example of FIG. 1D, which is a typical traditional contact electrode system arrangement, each sample area 151 is of a width corresponding to the distance 121 between rows 120 of FIG. 1C and each individual sample area 151 is of a length corresponding to the distance 131 between columns 130 of FIG. 1C. As a result, each sample area is distance 121 by distance 131 in dimensions or has an area of distance 131 by 121 square units.

In a typical configuration, distance 121 is 9" and distance 131 is 3." Consequently, typical moisture measurements are taken in sample areas of approximately 9"×3" simply because of the physical proximity and placement of contact electrodes 101.

Consequently, the typical traditional contact electrode system structure shown in FIG. 1C presents another problematic issue associated with traditional contact electrode systems. This issue arises given that the approximately 9"×3" dimensions of the sample areas 151 yields a of surface area of 27 square inches or so for each sample area 151. This is a very low "resolution" in that pockets of moisture of surface areas less than 27 square inches can be missed entirely or given more weight than is warranted by the actual physical dimensions of the moisture pocket. Consequently, with only 128 sample points for a typical 4' by 8' sheet, the moisture levels of each of the 128 samples must be averaged to determine, at best, an average moisture level of the entire veneer sheet or wood product being analyzed. As a result of this, and several other inherent limitations of traditional contact electrode systems, the moisture level of a given veneer sheet or other wood product can consistently only be determined within about a ±5% margin of error using traditional contact electrode systems. In addition, the exact location of pockets of moisture cannot be accurately determined using traditional contact electrode systems.

These relatively large margins of error associated with traditional contact electrode systems, and the inability to determine the exact location of pockets of moisture, results in the need to be very conservative when determining the potential use of a given veneer sheet or other wood product. Therefore, using traditional contact electrode systems, wood products, such as veneer sheets, are often not put to their most cost effective and efficient use simply to ensure that the ±5% margin of error does not result in inferior or unsafe wood products. Clearly, this is an inefficient use of a valuable natural resource and a problematic situation for both the producer of the wood products and the end customer who inevitably must pay a higher price to take these inefficiencies into account.

Another issue associated with traditional contact electrode systems is the fact that these systems rely on high voltages. Therefore, traditional contact electrode systems can represent a danger to workers and other equipment. Consequently, various barriers and safety systems must be put into place when implementing contact electrode systems. In addition, the many repairs that are associated with these systems due to the physical contact requirements discussed above require shutting down the production line and ensuring various safety procedures are implemented and adhered to before the problem can be fixed. This results in lost time and further production inefficiencies. Further, the production of the high-voltages necessary to operate traditional contact electrode systems requires significant energy which, in turn, adds to the cost of production and the cost of the product.

The second type of traditional systems used to detect moisture in wood products are Radio Frequency (RF) systems.

FIG. 2A is an illustration of one example of a prior art traditional RF moisture detection system 200.

Traditional RF moisture detection systems, such as traditional RF moisture detection system 200, rely on the generation of RF signals which are then transmitted using RF transmitters 205 onto the surface 203 of, and through, the veneer sheet 201 or other wood product to RF receivers 209. RF moisture detection systems do represent an improvement over traditional contact electrode systems in that the RF moisture detection systems do not require physical contact with the surface of veneer sheet or other wood product. However, the distance 207 between the source of RF energy 205 and the surface 203 of the veneer sheet 201 or other wood product, and the distance 208 between the RF receiver 209 and surface 204 of veneer sheet 201 (FIG. 2B) must be relatively small and precisely maintained to avoid interference and to obtain accurate results.

This is graphically illustrated in FIG. 2B which shows a side view of RF transmitter 205 positioned a distance 207 above surface 203 of veneer sheet 201 and RF receiver 209 positioned a distance 208 below a surface 204 of veneer sheet 201. Since distances 207 and 208 are often less than an inch, and veneer sheet 201 surfaces 203 and 204 are often rough and uneven, damage to the RF moisture detection system 200 and surfaces 203 and 204 of the veneer sheet 201 is still a frequently encountered problem as the veneer sheets move past/between the RF transmitter 205 and RF receiver 209.

FIG. 2C shows a graphic illustration of a typical arrangement of RF transmitters 205 over a surface 203 of a veneer sheet 201 moving in direction 220 via conveyor belts 221, thereby creating sample channels 1 through 8.

FIG. 2D shows a sample sheet 240 created using the RF transmitter arrangement shown in FIG. 2C. As seen in FIG. 2C, like traditional contact electrode systems, RF moisture detection systems are limited in the size of the sample 251 that can be tested on the surface of a veneer sheet or wood product. As seen in FIG. 2D, each sample 251 area is of dimensions "x" by "y." Traditionally, RF moisture detection systems utilize RF chambers that typically have a sample size of 12"×12." i.e., "x" is equal to 12" as is "y." Consequently, for a typical 4'×8' veneer sheet, the number of samples 251 is typically 32 with each sample representing 144 square inches of surface area.

Therefore, like traditional contact electrode systems, RF moisture detection systems have relatively low "resolution" in that pockets of moisture of surface areas less than 144 square inches can be missed entirely or given more weight than is warranted by the actual physical dimensions of the moisture pocket. Consequently, with only 32 sample points for a typical 4' by 8' sheet, the moisture levels of each of the 32 samples 251 must be averaged to determine, at best, an average moisture level of the entire veneer sheet or wood product being analyzed. As a result of this, and several other inherent limitations of RF moisture detection systems, the moisture level of a given veneer sheet or other wood product can consistently only be determined within about a ±7.5% margin of error using RF moisture detection systems. Further, the exact location of pockets of moisture cannot be accurately determined using RF moisture detection systems.

In addition, RF moisture detection systems are subject to interference from spurious RF energy that is often present in an industrial environment such as a wood processing plant.

Consequently, like traditional contact electrode systems, while traditional RF-based moisture detection systems do give some indication of the moisture level of a veneer or wood product being analyzed, the relatively large margins of error and inability to determine the exact location of pockets of moisture results in the need to be very conservative when determining the potential use of a given veneer layer or other wood product. Therefore, as with traditional contact electrode systems, the use of traditional RF-based moisture detection systems often results in wood products such as veneer sheets not being put to their most cost effective and efficient use simply to ensure that the ±7.5% margin of error does not result in structurally unsound product. As noted above, this is neither an ideal situation for the producer of the wood products or the end customer who inevitably must pay a higher price to take into account these inefficiencies.

What is needed is a technical solution to the long-standing technical problem of accurately and efficiently detecting moisture levels and moisture pocket locations in an entire sheet or surface of a wood product, such as veneer sheets. In addition, the technical solution needs to be capable of being implemented without significantly slowing down the production process or increasing the cost of the finished wood product.

SUMMARY

Embodiments of the present disclosure provide an effective and efficient technical solution to the technical problem of accurately and efficiently detecting moisture levels and moisture locations in an entire sheet or surface of a wood product, such as veneer sheets. In addition, the disclosed technical solution is capable of detecting the moisture levels of an entire surface of a wood product in a single pass. Consequently, the disclosed embodiments can be implemented without significantly slowing down the production process or increasing the cost of the finished wood product.

To this end, embodiments of the present disclosure utilize Near InfraRed (NIR) technology, including Near InfraRed/ Short Wave InfraRed (NIR/SWIR) cameras and detectors, to accurately identify moisture content and the specific locations of the moisture in a veneer sheet or other wood product. As discussed in more detail below, in some embodiments, a moisture level to greyscale mapping database is generated that maps moisture level to NIR image greyscale values for one or more wood products, such as, but not limited to, one or more types of veneer sheets. In one embodiment, the moisture level to greyscale mapping database includes mapping data obtained via controlled empirical methods.

In one embodiment, an NIR analysis station is provided. In one embodiment, the NIR analysis station includes one or more sources of illumination positioned to illuminate at least one surface of a veneer sheet or other wood product. In one embodiment, the NIR analysis station includes one or more NIR/SWIR cameras, hereafter referred to as simply NIR cameras, positioned to capture one or more NIR images of the illuminated surface of the veneer sheet or other wood product.

In one embodiment, a veneer sheet or other wood product to be analyzed is positioned in, or passed through, the NIR analysis station such that a surface of the veneer sheet or other wood product to be analyzed is illuminated by the one or more illumination sources. The one or more NIR cameras are then used to capture one or more NIR images of the illuminated surface of the veneer sheet or other wood product.

In one embodiment, the one or more NIR images of the illuminated surface of the veneer sheet or other wood product are converted to NIR greyscale images with different greyscale values indicating different moisture levels in the illuminated surface of the veneer sheet or other wood product.

In one embodiment, the greyscale values shown in the NIR greyscale images are processed using the moisture level to greyscale mapping database to identify moisture levels over the entire surface of the veneer sheet or other wood product analyzed.

In one embodiment, the veneer sheet or other wood product is then graded based on the identified moisture levels and their positions/locations over the entire surface of the veneer sheet or other wood product. In one embodiment, based, at least in part, on the grade assigned to the veneer sheet or other wood product being analyzed, one or more actions are taken with respect to the veneer sheet or other wood product.

As discussed in more detail below, in some embodiments, one or more machine learning based moisture level detection models are trained using NIR image data for one or more wood products along with various other production parameters and corresponding empirically determined moisture levels for the one or more wood products.

In one embodiment, an NIR analysis station is provided that includes one or more sources of illumination positioned to illuminate a surface of a wood product and one or more NIR cameras positioned to capture one or more NIR images of the illuminated surface of the wood product.

In one embodiment, a wood product to be analyzed is positioned, or passed through, the NIR analysis station such that a first surface of the wood product to be analyzed is illuminated by the one or more illumination sources.

In one embodiment, one or more NIR images of the illuminated first surface of the wood product are then captured using the one or more NIR cameras and the one or more NIR images of the illuminated first surface of the wood product are processed to generate NIR image data for the illuminated first surface of the wood product.

In one embodiment, the NIR image data for the illuminated first surface of the wood product is then provided to the one or more trained machine learning based moisture level detection models and moisture level prediction data for the wood product is obtained from the one or more trained machine learning based moisture level detection models.

In one embodiment, a grade is assigned to the wood product based on the moisture level prediction data for the wood product and, based, at least in part, on the grade assigned to the wood product, one or more actions are taken with respect to the wood product.

As discussed in more detail below, in some embodiments, a moisture level to greyscale mapping database is generated that maps moisture level to NIR image greyscale values for one or more wood products, such as, but not limited to, one or more types of veneer sheets. In one embodiment, the moisture level to greyscale mapping database includes mapping data obtained via controlled empirical methods.

In one embodiment, an NIR analysis station is provided. In one embodiment, the NIR analysis station includes one or more sources of illumination positioned to illuminate at least one surface of a veneer sheet or other wood product. In one embodiment, the NIR analysis station includes one or more NIR/SWIR cameras, hereafter referred to as simply NIR cameras, positioned to capture one or more NIR images of the illuminated surface of the veneer sheet or other wood product.

In one embodiment, a veneer sheet or other wood product to be analyzed is positioned in, or passed through, the NIR analysis station such that a surface of the veneer sheet or other wood product to be analyzed is illuminated by the one or more illumination sources. The one or more NIR cameras are then used to capture one or more NIR images of the illuminated surface of the veneer sheet or other wood product.

In one embodiment, the one or more NIR images of the illuminated surface of the veneer sheet or other wood product are converted to NIR greyscale images with different greyscale values indicating different moisture levels in the illuminated surface of the veneer sheet or other wood product.

In one embodiment, the greyscale values shown in the NIR greyscale images are processed using the moisture level to greyscale mapping database to identify moisture levels over the entire surface of the veneer sheet or other wood product analyzed.

In one embodiment, one or more visual image cameras are provided and positioned to capture visual images of the first surface of the wood product. In one embodiment, the one or more visual image cameras are used to capture one or more visual images of the first surface of the wood product.

In one embodiment, the one or more NIR greyscale images and the one or more visual images of the first surface of the wood product are processed to generate NIR greyscale and visual superimposed images of the first surface of the wood product indicating different moisture levels and proximity of visual elements in the first surface of the wood product.

In one embodiment, a grade is assigned to the wood product based on the identified moisture levels and proximate visual elements in the first surface of the wood product and based, at least in part, on the grade assigned to the wood product, taking one or more actions with respect to the wood product.

The disclosed embodiments utilize NIR cameras to scan the surface of a wood product for moisture and create an NIR image of the surface of the wood product. Since essentially each pixel of camera image data is a sample point, the resolution and accuracy of the moisture detection process is only limited by the number of pixels the camera has covering the field of view, e.g., the entire first surface of a wood product. Consequently, in the case where a 1.3 mega pixel camera is used there are essentially 1,300,000 individual measurement points on the surface of the wood product. Consequently, the use of NIR cameras as disclosed herein results in resolutions and accuracy that simply cannot be achieved using traditional moisture detection systems such as traditional contact electrode systems or RF moisture detection systems.

As noted, using traditional moisture detection systems such as traditional contact electrode systems or RF moisture detection systems accuracy levels are subject to, at best, ±5.0% or ±7.5% margin of error. This resulted in the need to be very conservative when determining the potential use of a given veneer sheet or other wood product and often resulted in wood products, such as veneer sheets, not being put to their most cost effective and efficient use simply to ensure that the ±5.0% or ±7.5% margin of error did not result in inferior or unsafe wood products.

In contrast, using the disclosed NIR camera-based systems, accuracy on the order of ±0.1% is readily achieved. Therefore, the highest value use of a given veneer sheet or other wood product can be accurately, and confidently determined so that the wood products, such as veneer sheets, can be put to their most cost effective and efficient use.

In addition, when, as disclosed herein, NIR cameras are used as the moisture detection mechanism, if greater or less resolution is deemed necessary, a higher or lower megapixel camera can be selected to achieve the desired resolution for the process. This can be accomplished in a relatively simple and quick camera switch out procedure. In addition, unlike tradition contact electrode and RF moisture detection systems, NIR camera placement with respect to the sample under analysis can be adjusted such that a quality image can be obtained as long as there is a clear field of view between the wood product surface and NIR camera. Horizontal, vertical, or angled placements have no impact on the functionality of the NIR camera. Further, combinations of NIR cameras and lenses can provide opportunities to perform measurements that are currently prohibitive due to the need for a conveyor section to convey the material through a sensing array of contact electrodes or RF instruments.

The use of NIR cameras, are disclosed herein, eliminates the need for any physical contact with the wood product by any part of the moisture detection device, or even the need for the moisture detection device, i.e., the NIR camera, to be close to the surface of a wood product. Not only does this fact eliminate wear and tear on both the sample taking device and the wood product, but, as discussed above, it allows for more flexible placement of the sample taking device, i.e., the NIR camera.

In addition, unlike RF moisture detection devices and contact electrodes, NIR cameras are virtually immune to static electricity or spurious RF emissions. Consequently, use of NIR cameras as disclosed herein is far more suitable for a physical production line environment.

Finally, unlike traditional contact electrode systems that require high voltages and represent a danger to workers, NIR technology has been determined to be safe, i.e., representing no hazards to workers or other devices, by several testing and safety agencies. Consequently, the use of the disclosed NIR based moisture detection systems results in a safer and more comfortable and efficient workplace and production floor.

As a result of these and other disclosed features, which are discussed in more detail below, the disclosed embodiments address the short comings of the prior art moisture detection systems and provide an effective and efficient technical solution to the technical problem of accurately and efficiently detecting moisture levels and locations in an entire sheet or surface of a wood product, such as veneer sheets or other wood products. In addition, the technical solution is capable of analyzing an entire surface of a wood product, such as a veneer sheet, in a single pass, i.e., with a single NIR image. Consequently, the disclosed embodiments can be implemented without significantly slowing down the production process or increasing the cost of the finished wood product.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1A:
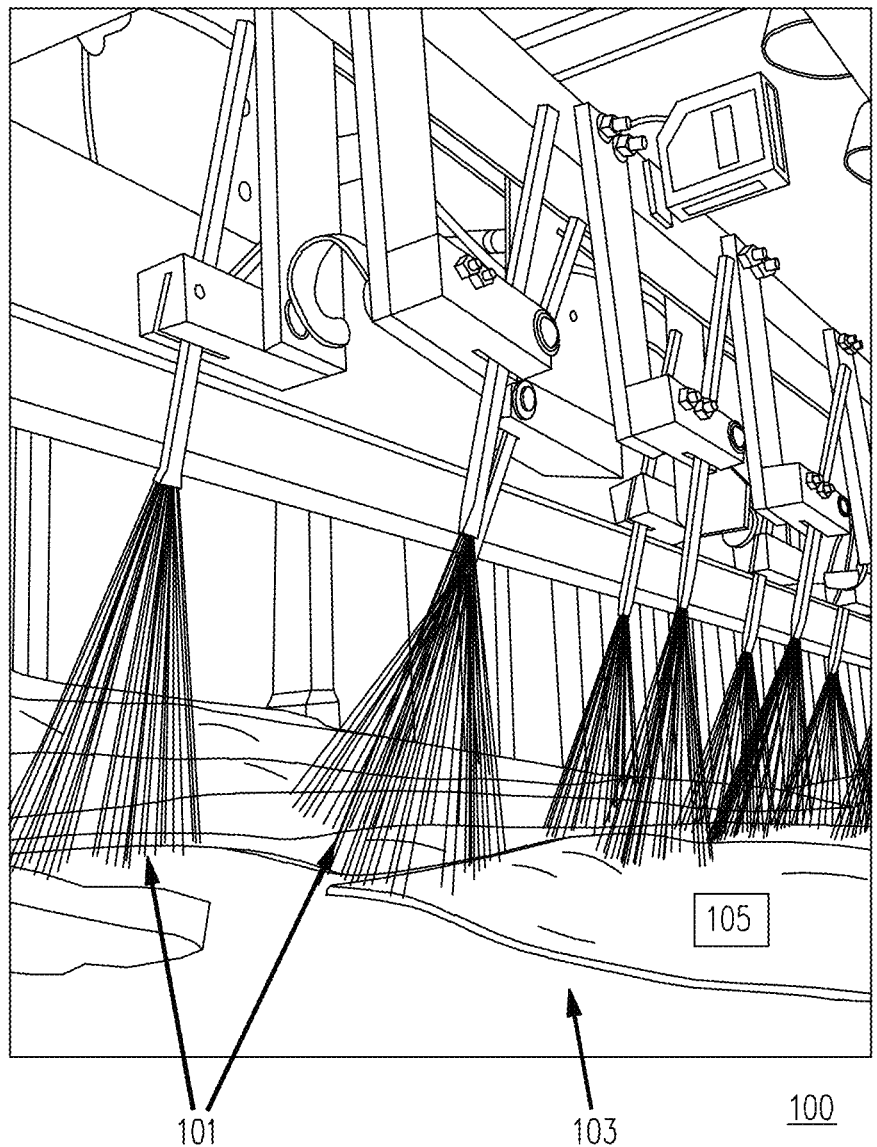
FIG. 1A is an illustration of one example of a prior art traditional contact electrode system.
Figure 1B:
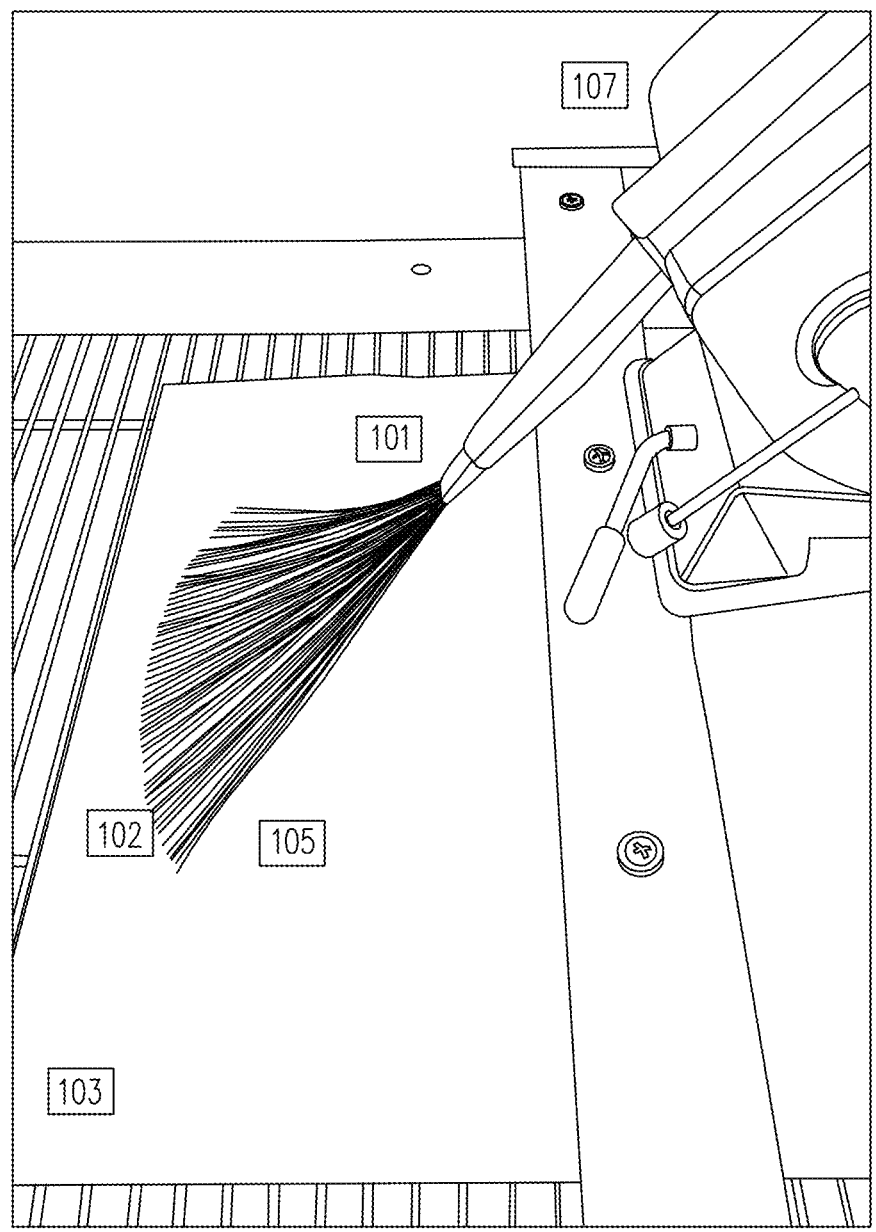
FIG. 1B is an illustration of one example of a contact electrodes of a prior art traditional contact electrode structure.
Figure 1C:
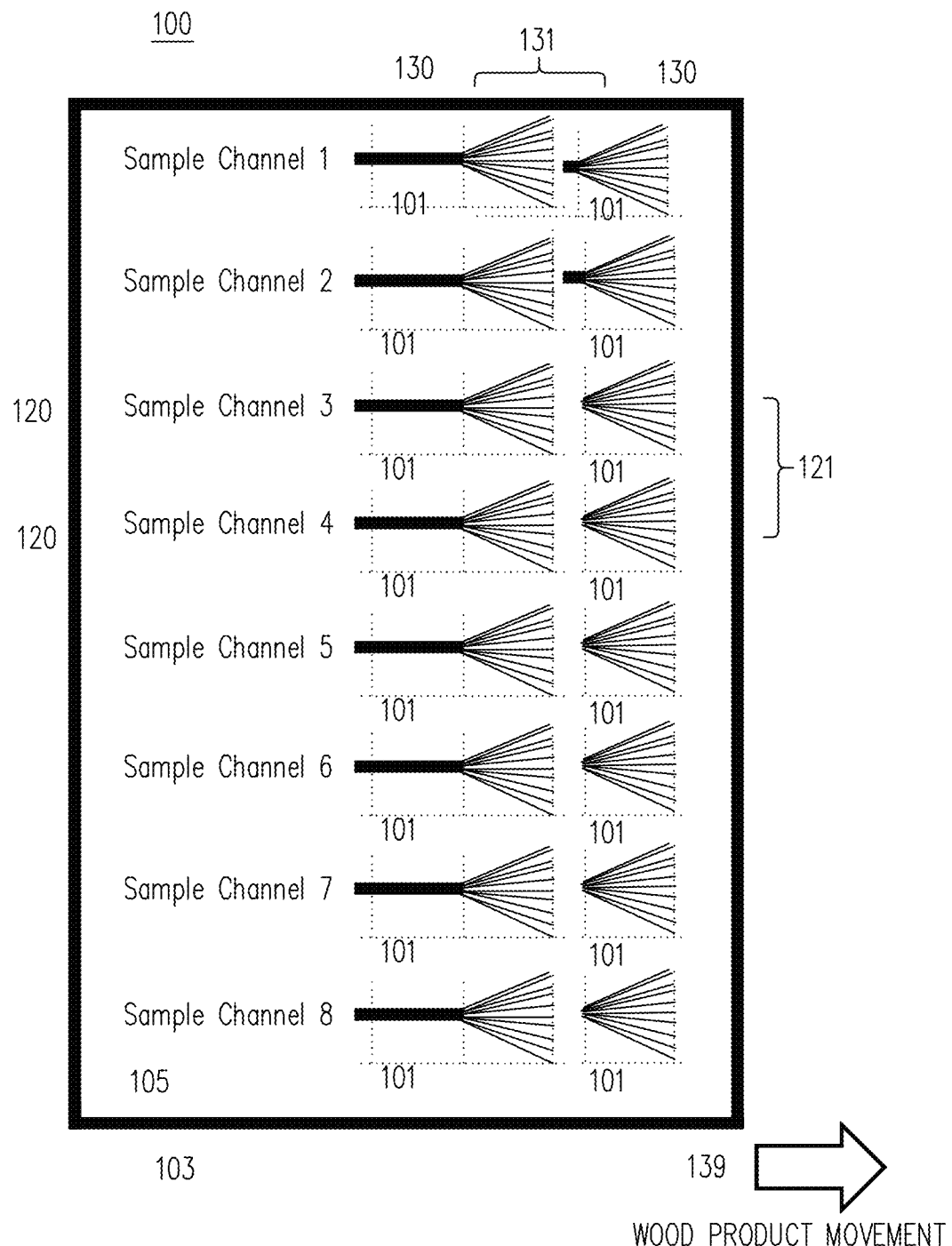
FIG. 1C is a graphical representation of the placement and spacing of individual contact electrodes using a typical traditional contact electrode system.
Figure 1D:
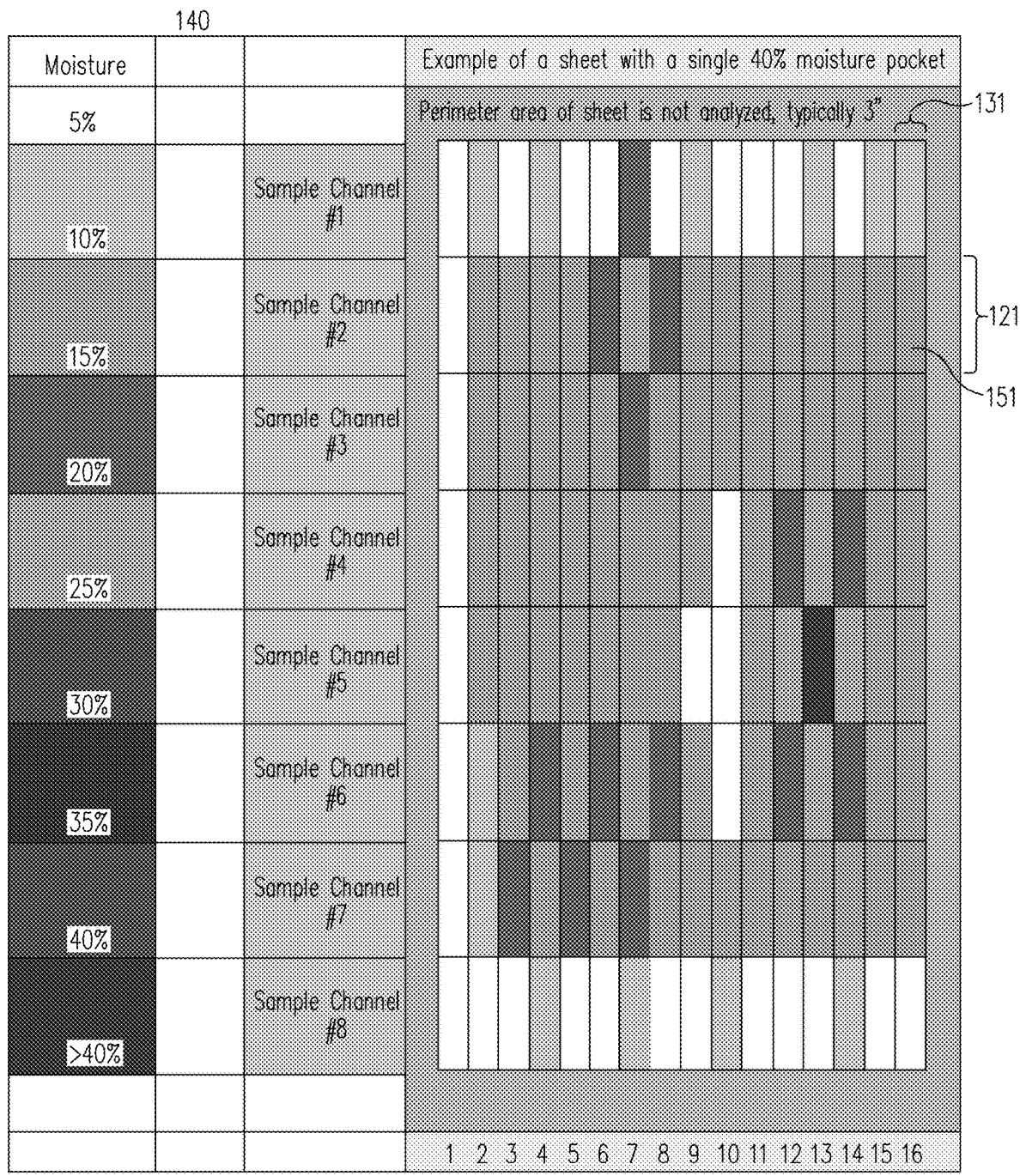
FIG. 1D shows a typical sample sheet generated using traditional contact electrode systems and the physical arrangement of FIG. 1C.
Figure 2A:
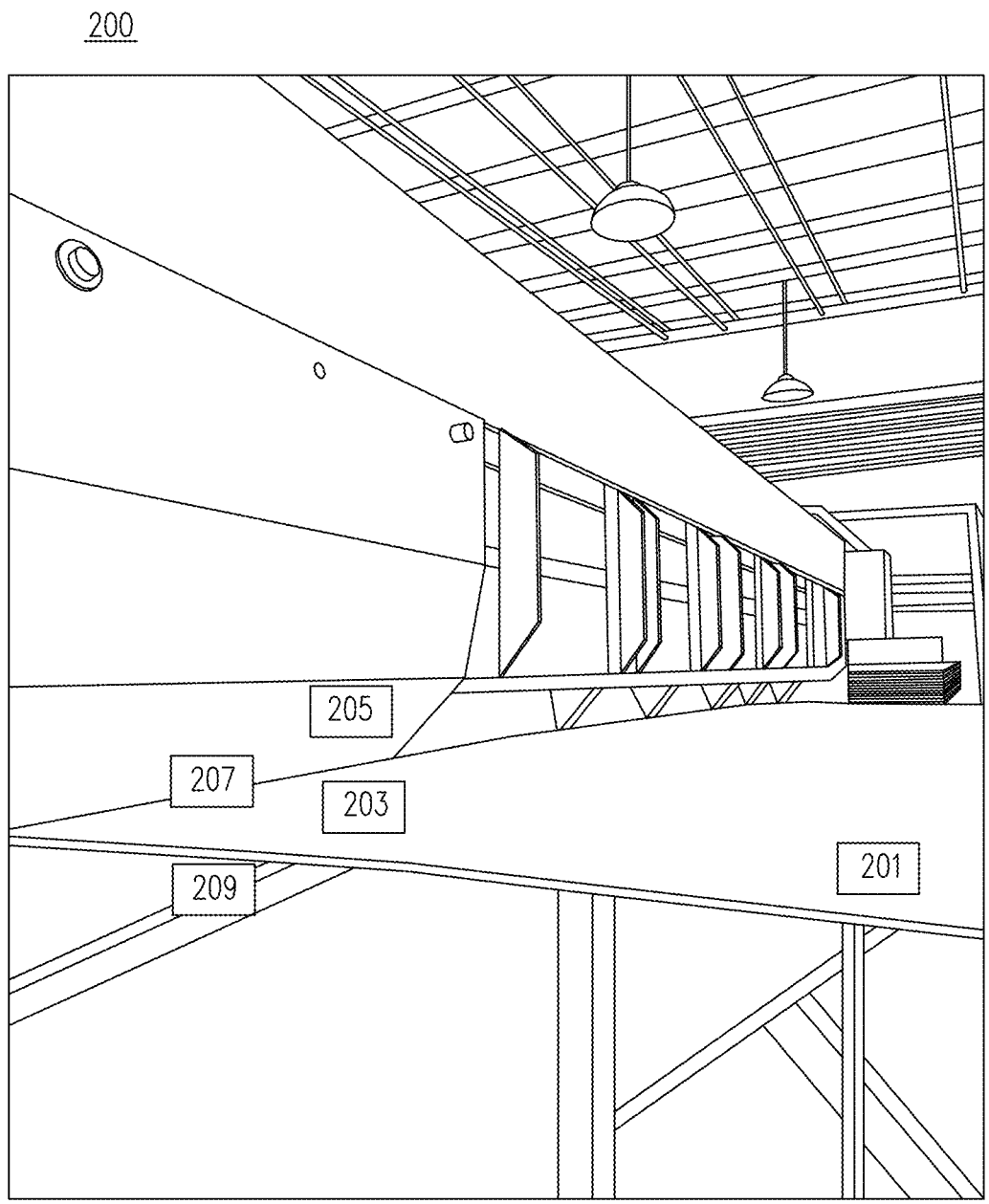
FIG. 2A is an illustration of one example of a prior art traditional RF moisture detection system.
Figure 2B:
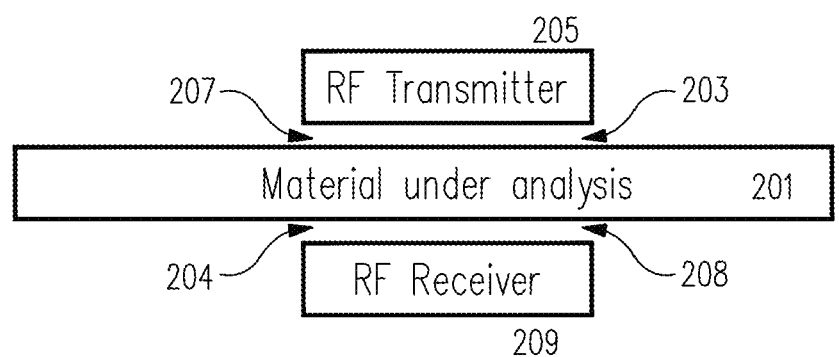
FIG. 2B shows a side view of an RF transmitter positioned above surface of a veneer sheet and an RF receiver positioned a distance below a surface of the veneer sheet.
Figure 2C:
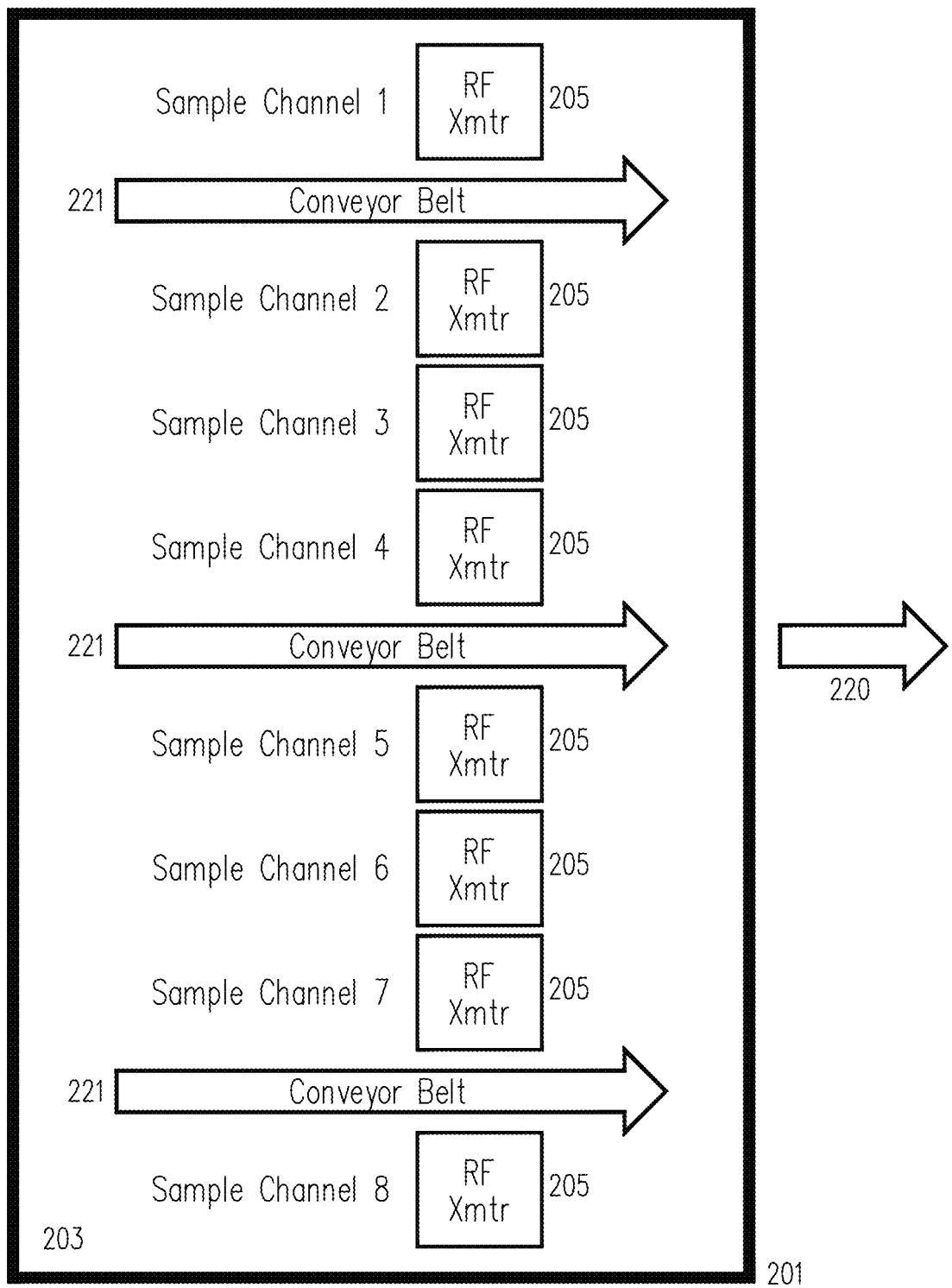
FIG. 2C shows a graphic illustration of a typical arrangement of RF transmitters over a surface of a veneer sheet moving via conveyor belts, thereby creating sample channels.
Figure 2D:
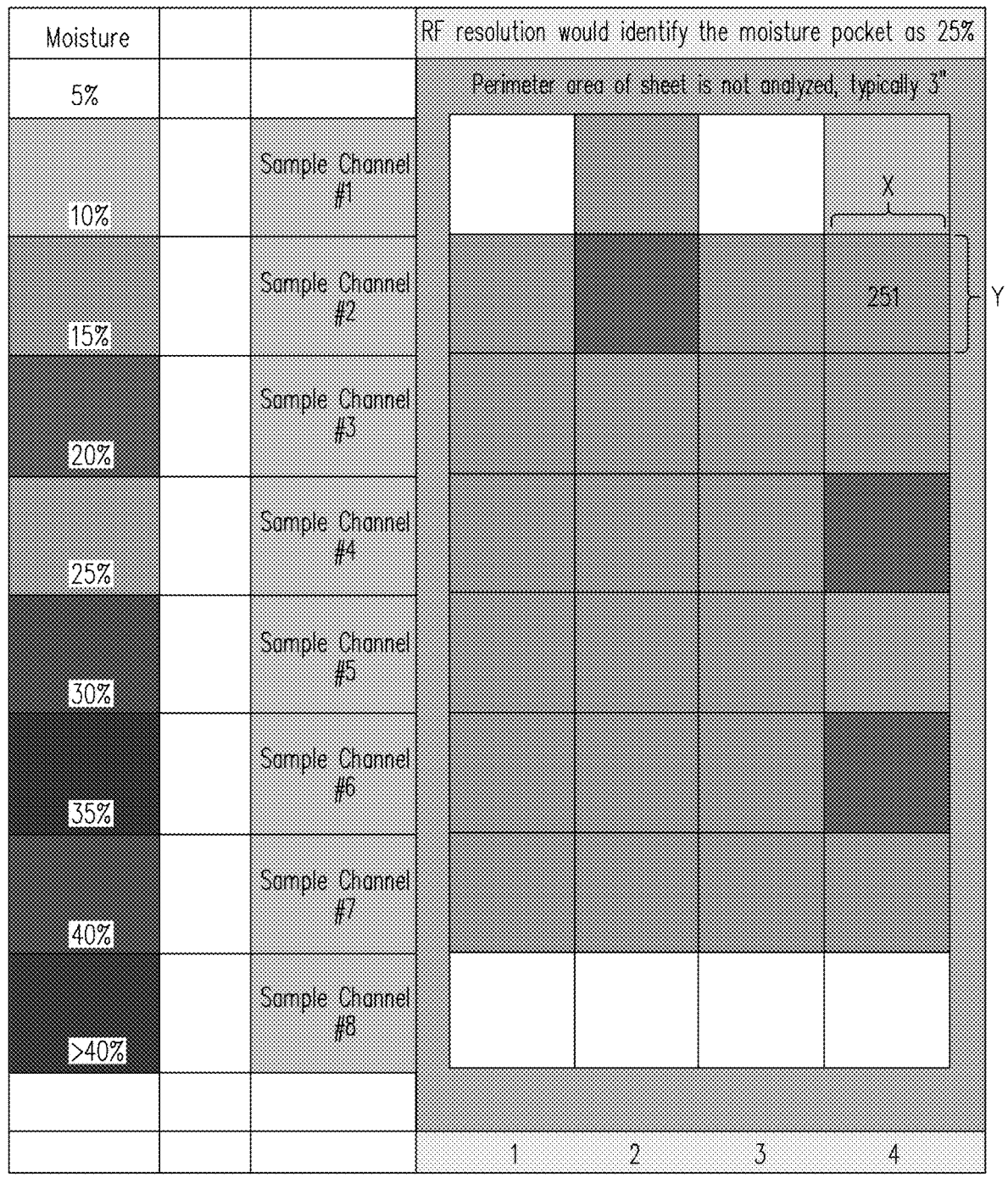
FIG. 2D shows a sample sheet created using the RF transmitter arrangement shown in FIG. 2C.

Common reference numerals are used throughout the figures and the detailed description to indicate like elements. One skilled in the art will readily recognize that the above figures are merely illustrative examples and that other architectures, modes of operation, orders of operation, and elements/functions can be provided and implemented without departing from the characteristics and features of the invention, as set forth in the claims.

DETAILED DESCRIPTION

Embodiments will now be discussed with reference to the accompanying figures, which depict one or more exemplary embodiments. Embodiments may be implemented in many different forms and should not be construed as limited to the embodiments set forth herein, shown in the figures, or described below. Rather, these exemplary embodiments are provided to allow a complete disclosure that conveys the principles of the invention, as set forth in the claims, to those of skill in the art.

The disclosed embodiments utilize NIR technology, including NIR cameras and detectors, to accurately identify moisture content and the specific locations of the moisture in a veneer sheet or other wood product surface.

As discussed in more detail below, in one embodiment, this is accomplished by providing a NIR analysis station including one or more illumination sources and one or more NIR cameras.

A wood product, such as a veneer sheet is then positioned in, and/or is passed through, the NIR analysis station. At the NIR analysis station an entire first surface of the veneer sheet or other wood product to be analyzed is illuminated by the one or more illumination sources and the one or more NIR cameras are used to capture one or more NIR images of the illuminated surface of the veneer sheet or other wood product.

The one or more NIR images of entire first surface of the veneer sheet or other wood product are then analyzed and moisture levels over the entire first surface of the veneer sheet or other wood product are identified. In one example, this is accomplished with the aid of a moisture level to greyscale mapping database containing empirical data. In another embodiment, this is accomplished using the greyscale mapping database containing empirical data and a greyscale to color mapping database. In another embodiment, this is accomplished using one or more machine learning based models.

Once the moisture levels over the entire first surface of the veneer sheet or other wood product are identified, a grade is assigned to the wood product based on the identified moisture levels for the wood product and based, at least in part, on the grade assigned to the wood product, one or more actions are taken with respect to the wood product.

The one or more actions can include one or more of: sorting the wood product into a bin/location associated with the grade assigned to the wood product; restricting the use of the wood product based on grade assigned to the wood product; rejecting the wood product based on the grade assigned to the wood product; sending the wood product back for further processing based on the grade assigned to the wood product; adjusting one or more processing parameters of a production line based on grades assigned to one or more wood products; adjusting drying temperatures on a production line based on grades assigned to one or more wood products; and adjusting drying times on a production line based on grades assigned to one or more wood products.

Consequently, disclosed herein is an effective and efficient technical solution to the technical problem of accurately and efficiently detecting moisture levels and moisture pockets in an entire sheet or surface of a wood product, such as veneer sheets or other wood products. In addition, since, in one embodiment, the disclosed embodiments use NIR cameras to take NIR images of an entire wood product surface the technical solution is capable of accurately analyzing an entire surface of a wood product, such as a veneer sheet, in a single pass. Consequently, the embodiments can be implemented without significantly slowing down the production process or increasing the cost of the finished wood product.

Figure 3A:
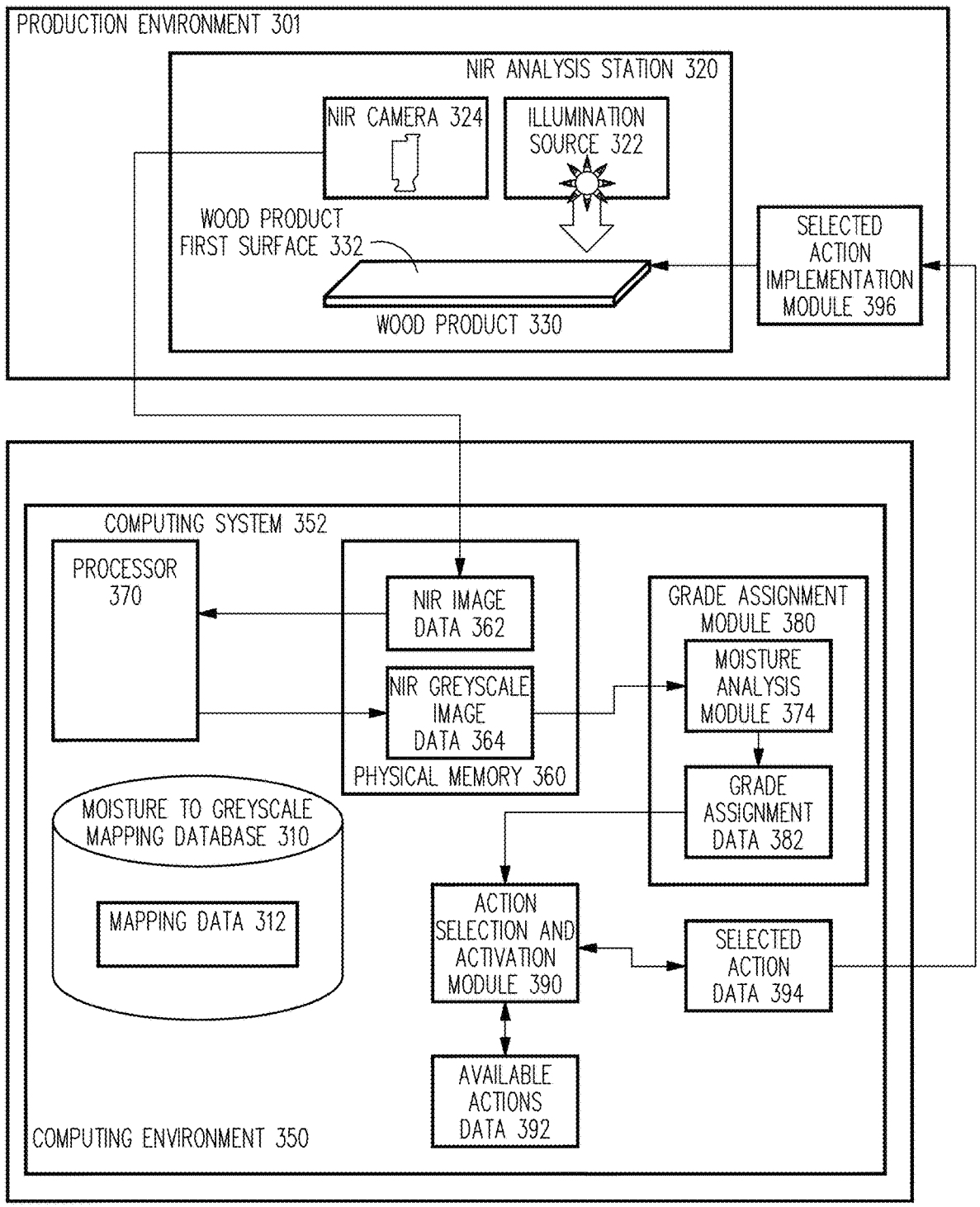
FIG. 3A is simplified block diagram of a system for detecting moisture levels in a wood product using NIR technology in accordance with one embodiment.

FIG. 3A is simplified block diagram of one embodiment of a system 300 for detecting moisture levels in a wood product using NIR technology in accordance with one embodiment.

In one embodiment, system 300 for detecting moisture levels in wood products includes a production environment 301 and a computing environment 350.

As seen in FIG. 3A, production environment 301 includes NIR analysis station 320 and selected action implementation module 396. As seen in FIG. 3A, NIR analysis station 320 includes one or more illumination sources, such as illumination source 322, positioned to illuminate a surface of a wood product. In various embodiments, the one or more illumination sources, such as illumination source 322, can include one or more LED light sources. In other embodiments, the one or more illumination sources, such as illumination source 322, can include, but are not limited to, halogen, halogen and tungsten light sources, or any other light sources, as discussed herein, and/or as known in the art at the time of filing, and/or as developed after the time of filing.

As seen in FIG. 3A, NIR analysis station 320 also includes one or more NIR cameras, such as NIR camera 324, positioned to capture NIR image data 362 representing one or more NIR images of the illuminated surface of the wood product. In one embodiment, the one or more NIR cameras, such as NIR camera 324, are adjustably positioned and adjustably focused to capture any desired one or more NIR images of the illuminated surface of the wood product.

As used herein, the terms Near InfraRed (NIR) and Short-Wave InfraRed (SWIR) are used interchangeably to include wavelength in the range of 750 nanometers (nm) to 3500 nm. In addition, all stated wave lengths herein are assumed to include values within 10% of the stated value.

As seen in FIG. 3A, and as discussed below, a wood product 330 to be analyzed in the NIR analysis station 320 is positioned in NIR analysis station 320. In various embodiments, the wood product 330 can be any wood product as discussed herein, and/or as known in the art at the time of filing and/or as becomes known after the time of filing. In one embodiment, the wood product 330 to be analyzed is a veneer sheet.

In one embodiment, the wood product 330 to be analyzed is positioned such that a wood product first surface 332 of the wood product 330 to be analyzed is illuminated by the illumination source 322 and the entire wood product first surface 332 is within view and focus of NIR camera 324. In one embodiment, the wood product 330 is positioned in the NIR analysis station 320 by passing the wood product 330 through the NIR analysis station 320 on a conveyor system (not shown in FIG. 3A but shown as 321 in FIG. 3B and discussed below).

In various embodiments, the one or more NIR cameras, such as NIR camera 324, can be of any resolution desired. As noted above, when the one or more NIR cameras, such as NIR camera 324, are used to scan the wood product first surface 332 of a wood product 330 for moisture and create an NIR image 362 of the wood product first surface 332, essentially each pixel generated by NIR camera 324 is a sample point. Consequently, the resolution and accuracy of the moisture detection process is only limited by the number of pixels the NIR camera 324 has covering the field of view, e.g., the entire wood product first surface 332 of wood product 330. Consequently, in the case where NIR camera 324 is a 1.3 mega pixel camera, there are essentially 1,300,000 individual measurement points on the wood product first surface 332. Consequently, using NIR cameras, such as NIR camera 324, results in resolutions and accuracy that simply cannot be achieved using traditional moisture detection systems such as traditional contact electrode systems or RF moisture detection systems.

As seen in FIG. 3A, computing environment 350 includes computing system 352. As seen in FIG. 3A, in one embodiment, computing system 352 includes moisture to greyscale mapping database 310 containing mapping data 312 that maps moisture level to Near InfraRed (NIR) image greyscale values for one or more wood products.

Using NIR images, extremely granular differences in moisture levels can be detected. In general, locations with different levels of moisture absorb/reflect different amounts of NIR radiation at specific frequencies. For moisture detection the NIR frequencies of 1450 nm, 1900 nm and 2400 nm are found to yield the best results.

In operation, when NIR radiation of a given frequency is applied to a wood product first surface 332 of wood product 330, more NIR energy is absorbed at locations having moisture than those that are dry, with greater amounts of NIR energy being absorbed at locations having greater moisture. When the NIR camera 324 takes an image of the wood product first surface 332, the NIR camera 324 picks up the NIR energy reflected off wood product first surface 332. Consequently, when the NIR camera 324 takes an image of the wood product first surface 322, the areas of moisture, which absorb more NIR energy and therefore reflect less NIR energy, appear darker than dry areas. In addition, the more moisture that is present the darker the area appears because less NIR energy is reflected to be captured by the NIR camera 324.

Using this fact, NIR image data 362 captured by the NIR camera 324 can be processed into NIR greyscale image data 364. Greyscale images can be of varying resolution, or bit, types. A 16-bit integer greyscale image provides 65535 available tonal steps from 0 (black) to 65535 (white). A 32-bit integer greyscale image theoretically will provide 4,294,967,295 tonal steps from 0 (black) to 4294967295 (white). Converting an NIR image based on these number of greyscale tonal steps results in a margin of error of significantly less than 0.1%. This is in sharp contrast to the ±7.5% margin of error obtained using traditional moisture detection systems such as traditional contact electrode systems or RF moisture detection systems.

Using these facts, in one embodiment, the mapping data 312 is obtained through one or more empirical and/or manual processes. For instance, in one embodiment, sample wood products are first dried in a kiln or similar environment while the weight of the sample wood product is monitored. As the sample wood product dries, i.e., loses moisture, the weight of the sample wood product deceases. Once the weight of the wood product stabilizes for a defined period, such as 24 hours, the sample wood product is determined to contain minimal moisture.

Then the sample wood product is brought up in moisture content in defined increments, such as one percent of the dry sample wood product weight. At each increment, an NIR image of the sample wood product is taken and the greyscale value at that increment of moisture is determined. The greyscale value determined is then correlated to the specific moisture level at that increment.

This process is continued for multiple increments until a maximum moisture content is obtained and greyscale data for each increment is determined and correlated to the respective moisture content increment. In this way, mapping data 312 mapping each specific moisture content to specific greyscale values is generated for the sample wood product. The process can then be repeated for different wood products, different types of wood, and under varying parameters and conditions.

As seen in FIG. 3A, computing system 352 also includes physical memory 360. In one embodiment, the physical memory 360 includes NIR image data 362 representing one or more NIR images of the illuminated wood product first surface 332 of the wood product 330 captured using NIR camera 324.

As seen in FIG. 3A, in one embodiment, computing system 352 includes one or more processors 370 for processing the NIR image data representing one or more NIR images of the illuminated wood product first surface 332 of the wood product 330 to generate NIR greyscale image data 364 indicating different moisture levels in the illuminated wood product first surface 332 of the wood product 330.

In one embodiment, processor 370 processes the NIR greyscale image data 364 using the mapping data 312 from moisture to greyscale mapping database 310 to identify moisture levels for the wood product first surface 332 of the wood product 330.

As seen in FIG. 3A, in one embodiment, computing system 352 includes a grade assignment module 380 for assigning a grade to the wood product 330 based on the identified moisture levels for the wood product first surface 332. As seen in FIG. 3A, grade assignment module 380 includes moisture analysis module 374 which, along with processor 370, processes the NIR greyscale image data 364 using the mapping data 312 from moisture to greyscale mapping database 310 data to identify moisture levels for the wood product first surface 332 of the wood product 330. As a result of the processing by moisture analysis module 374 and processor 370, grade assignment data 382 is generated.

As seen in FIG. 3A, in one embodiment, grade assignment data 382 is provided to action selection and activation module 390 which selects an appropriate action of the actions represented in available actions data 392 based, at least in part on the grade indicated by grade assignment data 382. As seen in FIG. 3A, in one embodiment, the determined appropriate action is represented by selected action data 394.

As seen in FIG. 3A, in one embodiment, selected action data 394 is forwarded to an action activation module such as selected action implementation module 396 in production environment 301 to initialize one or more actions with respect to the wood product 330 based, at least in part, on the grade represented by grade assignment data 382 and assigned to the wood product 330 by action selection and activation module 390.

In one embodiment, one or more actions that can be taken represented in available actions data 392 include, but are not limited to: sorting the wood product 330 into a bin or location associated with the grade represented by grade assignment data 382 and assigned to the wood product 330; restricting the use of the wood product 330 based on the grade represented by grade assignment data 382 and assigned to the wood product 330; rejecting the wood product 330 based on the grade represented by grade assignment data 382 and assigned to the wood product 330; sending the wood product 330 back for further processing based on the grade represented by grade assignment data 382 and assigned to the wood product 330; adjusting one or more processing parameters of a production line in production environment 301 based, at least in part, on the grade represented by grade assignment data 382 and assigned to the wood product 330 and/or the grades assigned other wood products; adjusting drying temperatures on a production line in production environment 301 based, at least in part, on grade represented by grade assignment data 382 and assigned to the wood product 330 and/or the grades assigned other wood products; adjusting drying times on a production line in production environment 301 based, at least in part, on grade represented by grade assignment data 382 and assigned to the wood product 330 and/or the grades assigned other wood products; and selecting a type and amounts of glues used on a production line in production environment 301 based, at least in part, on grade represented by grade assignment data 382 and assigned to the wood product 330 and/or the grades assigned other wood products.

As a specific illustrative example a signal representing a grade assigned to the wood product 330 and/or the grades assigned other wood products can be provided to a wood product gluing station (not shown) in a production line so that a glue appropriate to adhere wood products having the assigned grade can be selected and made available to glue the wood product when it reaches the gluing station.

Figure 3B:
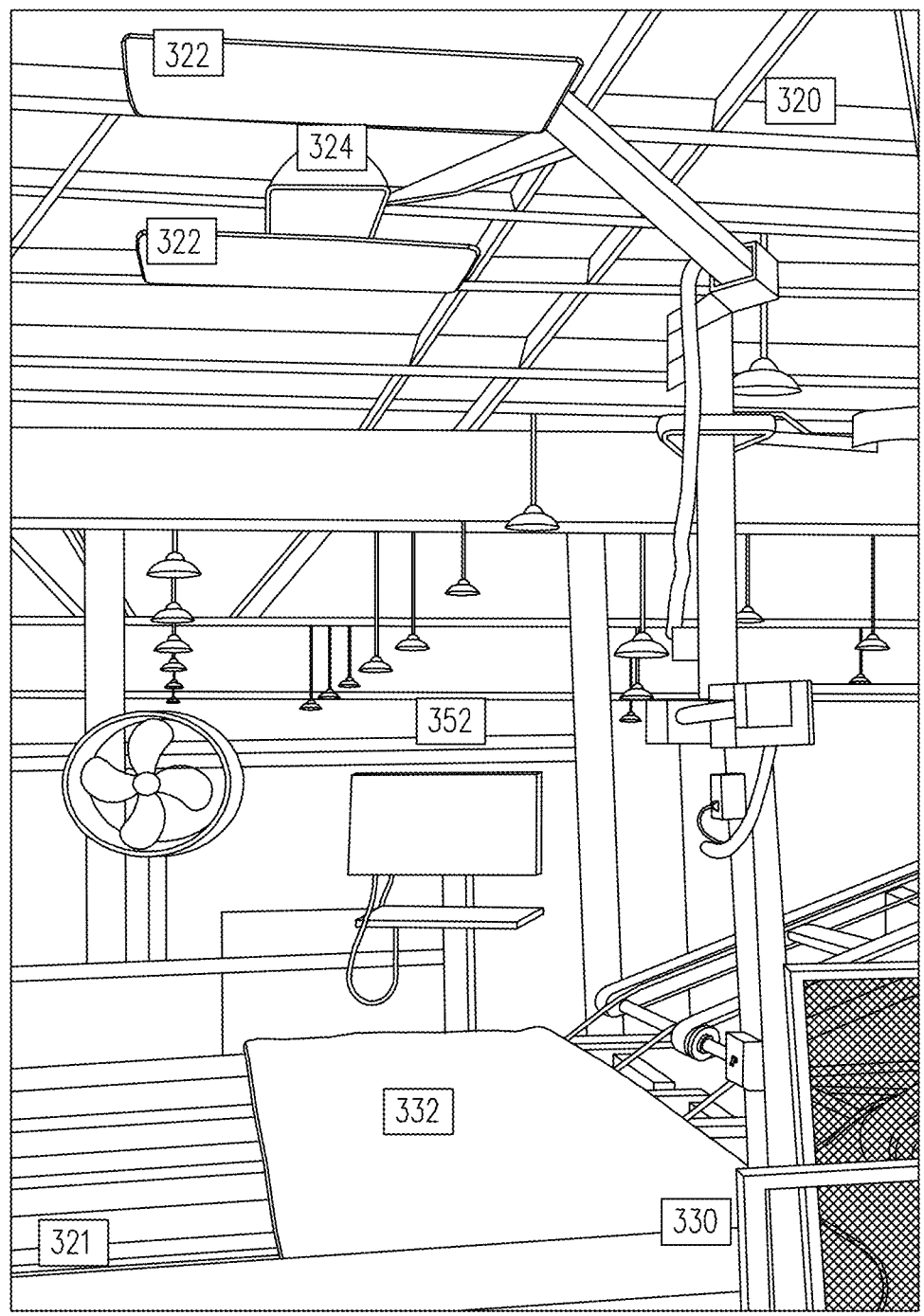
FIG. 3B shows one example of a physical system for detecting moisture levels in a wood product using NIR technology in accordance with one embodiment.

FIG. 3B shows one example of one embodiment of a physical system layout for detecting moisture levels in a wood product using NIR technology in accordance with one embodiment.

Referring to FIGS. 3A and 3B together, shown in FIG. 3B is a specific illustrative example of one embodiment of a physical production environment 301. As seen in FIG. 3B, in this in this specific illustrative example, production environment 301 includes NIR analysis station 320 and computing system 352.

As seen in FIG. 3B, NIR analysis station 320 includes illumination sources 322, in this specific illustrative embodiment two LED light sources, and NIR camera 324.

As seen in FIG. 3B, wood product 330, in this specific illustrative example a veneer sheet, is passed through NIR analysis station 320 via conveyor system 321 such that wood product first surface 332 is illuminated by illumination source 322. Then NIR camera 324 captures NIR image data 362 and forwards this data to computing system 352 for processing as discussed above.

Those of skill in the art will ready recognize that the specific illustrative examples of one embodiment of a production environment 301 and components shown in FIGS. 3A and 3B are but specific examples of numerous possible production environments and arrangement of physical components. Consequently, the specific illustrative example of embodiments of a production environment 301 and components shown in FIGS. 3A and 3B is not intended to limit the scope of the invention as set forth in the claims below.

Figure 4A:
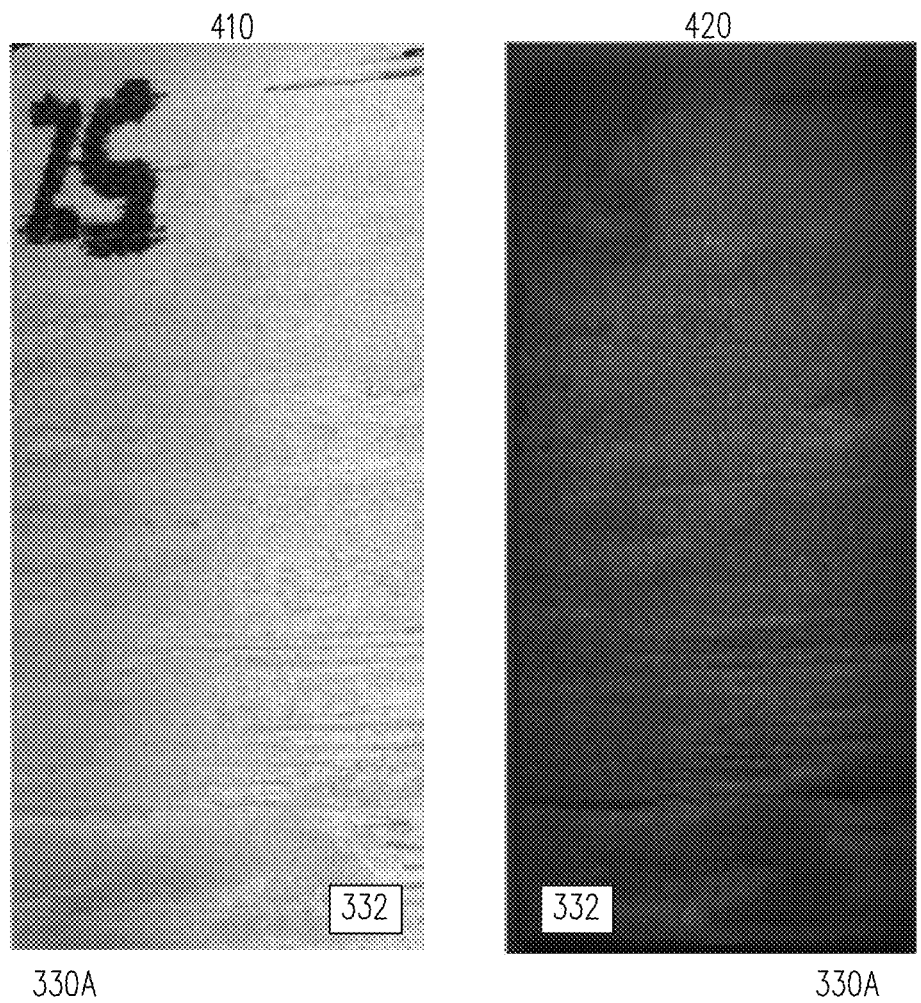
FIG. 4A shows a first surface of a dry veneer sheet as seen in a visual image of the dry veneer sheet and as seen in an NIR greyscale image of the dry veneer sheet.
Figure 4B:
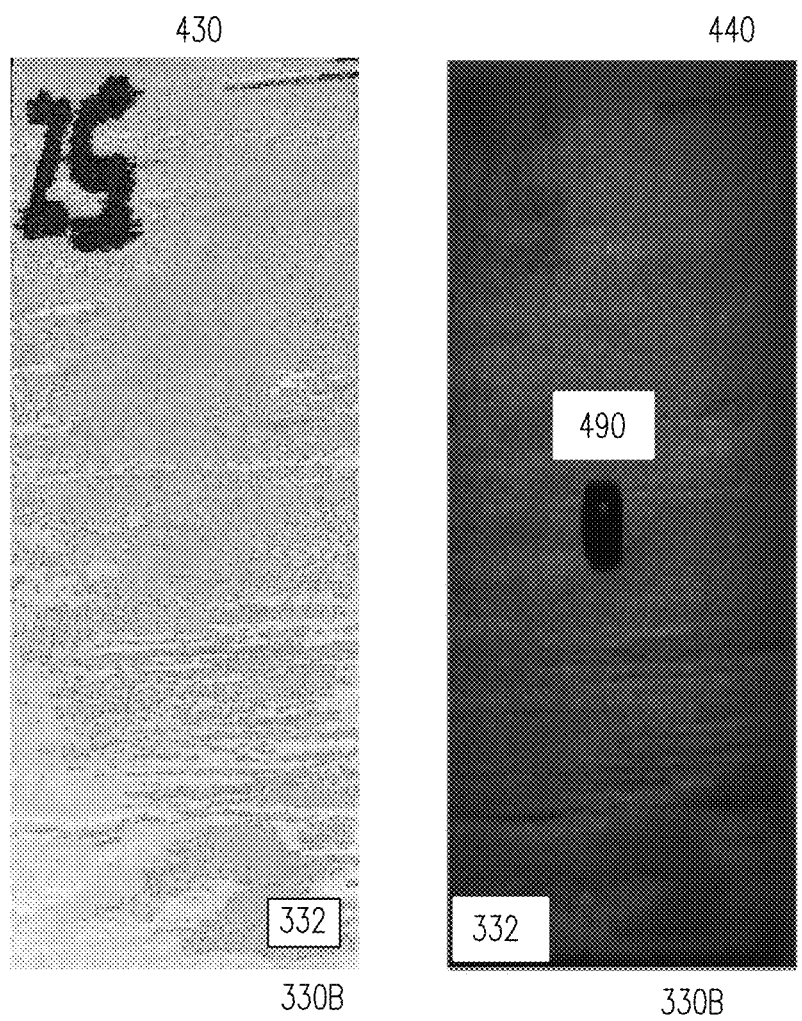
FIG. 4B shows a first surface of a veneer sheet, including a small moisture pocket, as seen in a visual image of the veneer sheet and as seen in an NIR greyscale image of the veneer sheet.
Figure 4C:
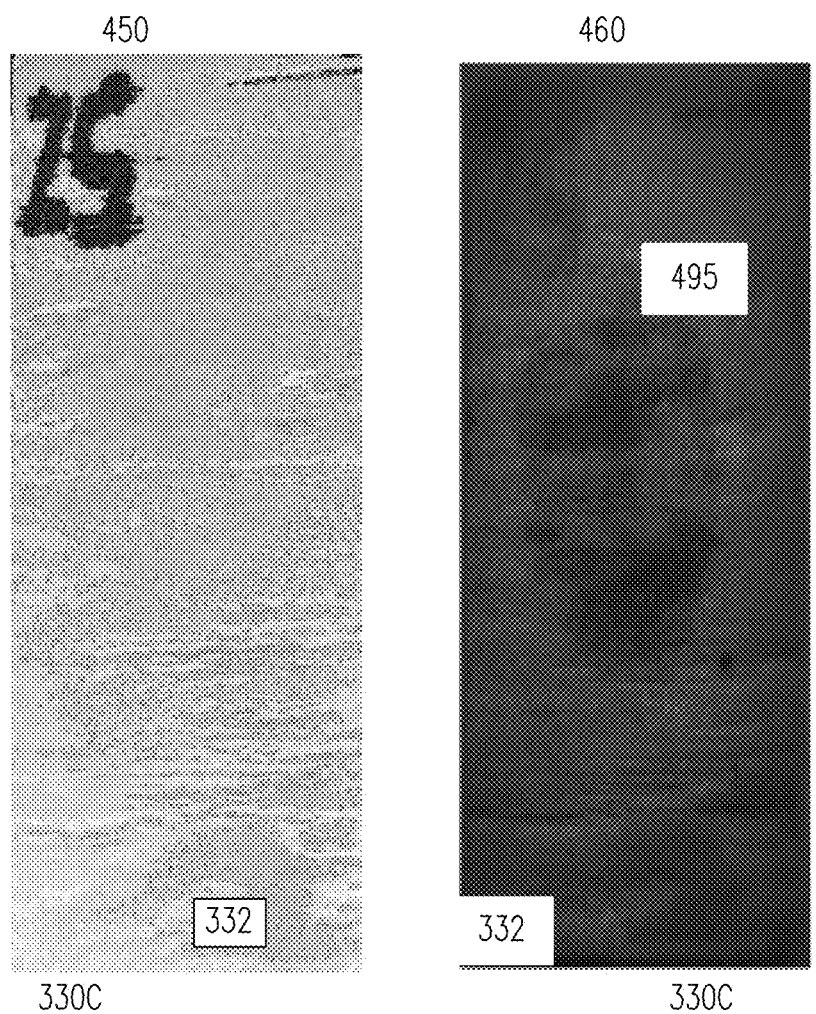
FIG. 4C shows a first surface of a veneer sheet, including a larger moisture pocket, as seen in a visual image of the veneer sheet and as seen in an NIR greyscale image of the veneer sheet.

FIGS. 4A, 4B, and 4C are specific illustrative examples of the operation of part of the system 300 for moisture detection of FIG. 3A. FIG. 4A shows a first surface 332 of a veneer sheet 330A as seen in a visual image 410 of the veneer sheet 330A and as seen in an NIR greyscale image 420 of the veneer sheet 330A. In the example of FIG. 4A, veneer sheet 330A has an average moisture level that is less than 5% and is therefore considered a dry veneer sheet.

It is worth noting that visual image 410 and NIR greyscale image 420 can be images of the entire wood product first surface 332 of veneer sheet 330A, i.e., can be a 4'×8' sample. In addition, as noted above, using a standard 1.3 mega pixel camera to obtain NIR greyscale image 420 of the entire wood product first surface 332 of veneer sheet 330A there are as many as 1,300,000 data points, i.e., each pixel is a data point. This, in turn, gives rise to very high resolution and is in sharp contrast to the 128 9"×3" samples of traditional contact electrode systems or 32 12"×12" samples of traditional RF systems that, as discussed above, yielded ±5.0% or ±7.5% margins of error, respectively.

As seen in FIG. 4A, the visual image 410 of the wood product first surface 332 of veneer sheet 330A is relatively uniform in appearance and coloration, i.e., no moisture can be readily detected visually in visual image 410 of the wood product first surface 332 of veneer sheet 330A. Likewise, since in this specific example veneer sheet 330A is a dry veneer sheet, the NIR greyscale image 420 of wood product first surface 332 of veneer sheet 330A is also relatively uniform in appearance and greyscale coloration.

FIG. 4B shows a first surface 332 of a veneer sheet 330B as seen in a visual image 430 of the veneer sheet 330B and as seen in an NIR greyscale image 440 of the veneer sheet 330B. In the example of FIG. 4B, veneer sheet 330B has an average moisture level that is less than 6% but includes a very high moisture pocket 490.

It is again worth noting that visual image 430 and NIR greyscale image 440 can be images of the entire wood product first surface 332 of veneer sheet 330B, i.e., can be a 4'×8' sample. In addition, as noted above, using a standard 1.3 mega pixel camera to obtain NIR greyscale image 440 of the entire wood product first surface 332 of veneer sheet 330B there are as many as 1,300,000 data points, i.e., each pixel is a data point. This, in turn, gives rise to resolutions unheard of using traditional moisture detection systems and accuracy previously unknown in the art.

This is in sharp contrast to the 128 9"×3" samples of traditional contact electrode systems or the 32 12"×12" samples of traditional RF systems that, as discussed above, yielded ±5.0% or ±7.5% margins of error, respectively. Indeed, using these traditional moisture detection systems, very high moisture pocket 490 could easily be missed or determined to be larger than it actually is because of these large sample sizes and large margins of error.

As seen in FIG. 4B, the visual image 430 of the wood product first surface 332 of veneer sheet 330B is relatively uniform in visual appearance and coloration, i.e., no moisture can be readily detected visually in visual image 430 of the wood product first surface 332 of veneer sheet 330B. However, in this specific example, NIR greyscale image 440 of wood product first surface 332 of veneer sheet 330B clearly shows very high moisture pocket 490 as a dark region of a higher greyscale value. Consequently, though virtually invisible to the eye, high moisture pocket 490 can readily be seen/detected in NIR greyscale image 440.

According to the disclosed embodiments, the level of moisture in very high moisture pocket 490 can then be determined by mapping the NIR greyscale image data 364 representing NIR greyscale image 440 and using the mapping data 312 from moisture to greyscale mapping database 310 to identify moisture levels for very high moisture pocket 490 and the wood product 330B.

Grade assignment module 380 can then assign a grade to the wood product 330B based on the identified moisture levels for very high moisture pocket 490 and the wood product 330B. As discussed above, action selection and activation module 390 can then select an appropriate action based, at least in part, on the grade indicated by grade assignment data 382.

FIG. 4C shows a first surface 332 of a veneer sheet 330C as seen in a visual image 450 of the veneer sheet 330C and as seen in an NIR greyscale image 460 of the veneer sheet 330C. In the example of FIG. 4C, veneer sheet 330C has an average moisture level that is less than 10% but includes a high moisture pocket 495.

As seen in FIG. 4C, the visual image 450 of the wood product first surface 332 of veneer sheet 330C is still relatively uniform in visual appearance and coloration, i.e., no moisture can be readily detected visually in visual image 450 of the wood product first surface 332 of veneer sheet 330C. However, in this specific example, NIR greyscale image 460 of wood product first surface 332 of veneer sheet 330C clearly shows high moisture pocket 495 as a dark region of a higher greyscale value than the surrounding areas. Consequently, though virtually invisible to the eye, high moisture pocket 495 can readily be seen/detected in NIR greyscale image 460.

According to the disclosed embodiments, the level of moisture in high moisture pocket 495 can then be determined by mapping the NIR greyscale image data 364 representing NIR greyscale image 460 and using the mapping data 312 from moisture to greyscale mapping database 310 to identify moisture levels for high moisture pocket 460 and wood product 330C.

Grade assignment module 380 can then assign a grade to the wood product 330C based on the identified moisture levels for high moisture pocket 495 and the wood product 330C. Action selection and activation module 390 can then select an appropriate action based, at least in part, on the grade indicated by grade assignment data 382.

Those of skill in the art will ready recognize that the specific illustrative examples of one embodiment of FIGS. 3A, 4A, 4B, and 4C are but specific examples of numerous possible production environments, arrangement of components, and images. Consequently, the specific illustrative examples of one embodiment shown in FIGS. 3A, 4A, 4B, and 4C are not intended to limit the scope of the invention as set forth in the claims below.

As a specific illustrative example of potential variations, in various embodiments, the NIR analysis station 320 can include one or more illumination sources 322 positioned to illuminate two or more surfaces of a wood product and one or more NIR cameras 324 positioned to capture one or more NIR images of the two or more illuminated surfaces of the wood product.

As a further specific illustrative example of variations possible, additional input data can be considered such as current ambient temperature and humidity. The combination of these parameters can be analyzed by an AI/ML algorithm to further refine the control process for material drying optimization and overall process efficiency.

As a another illustrative example of variations possible, multiple NIR cameras can be placed at one or more locations relative to the wood product to capture an image of the entire wood product or a portion of the wood product being subjected to moisture testing; such as at one or more of (i) above a wood product; (ii) below a wood product; (iii) at one or both sides of the wood product and/or at a position to capture an image of the product at an angle, such as at an angle of 20° to 45° (e.g. 30°) from either above or below the wood product or both. The multiple images captured from each of these cameras can be combined to form a composite image. This can smooth out any variations in detected moisture content from the actual moisture content that could be detected by capturing an image only from a single angle.

As another illustrative example of variations possible, multiple NIR cameras can be used and operated, for example, at respective different wavelengths from one another within this NIR range to provide more information about the moisture content of the wood product being analyzed. A specific more desirable wavelength at which the NIR cameras can be operated can be at one or more wavelengths in the range of, or in the range of about, from 1350 nm to 1550 nm. In some examples, the NIR camera can operate at a wavelength in the range of, or in the range of about, from 1400 nm to 1450 nm.

These and numerous other variations are possible and contemplated by the inventors to be within the scope of the invention as set forth in the claims below.

FIG. 3B shows one example of one embodiment of a physical system layout for detecting moisture levels in a wood product using NIR technology in accordance with one embodiment.

Those of skill in the art will ready recognize that the specific illustrative example of one embodiment of a physical production environment 301 and components shown in FIG. 3B is but one example of numerous possible production environments and arrangement of physical components. Consequently, the specific illustrative example of one embodiment of a physical production environment 301 and components shown in FIG. 3B is not intended to limit the scope of the invention as set forth in the claims below.

Figure 5:
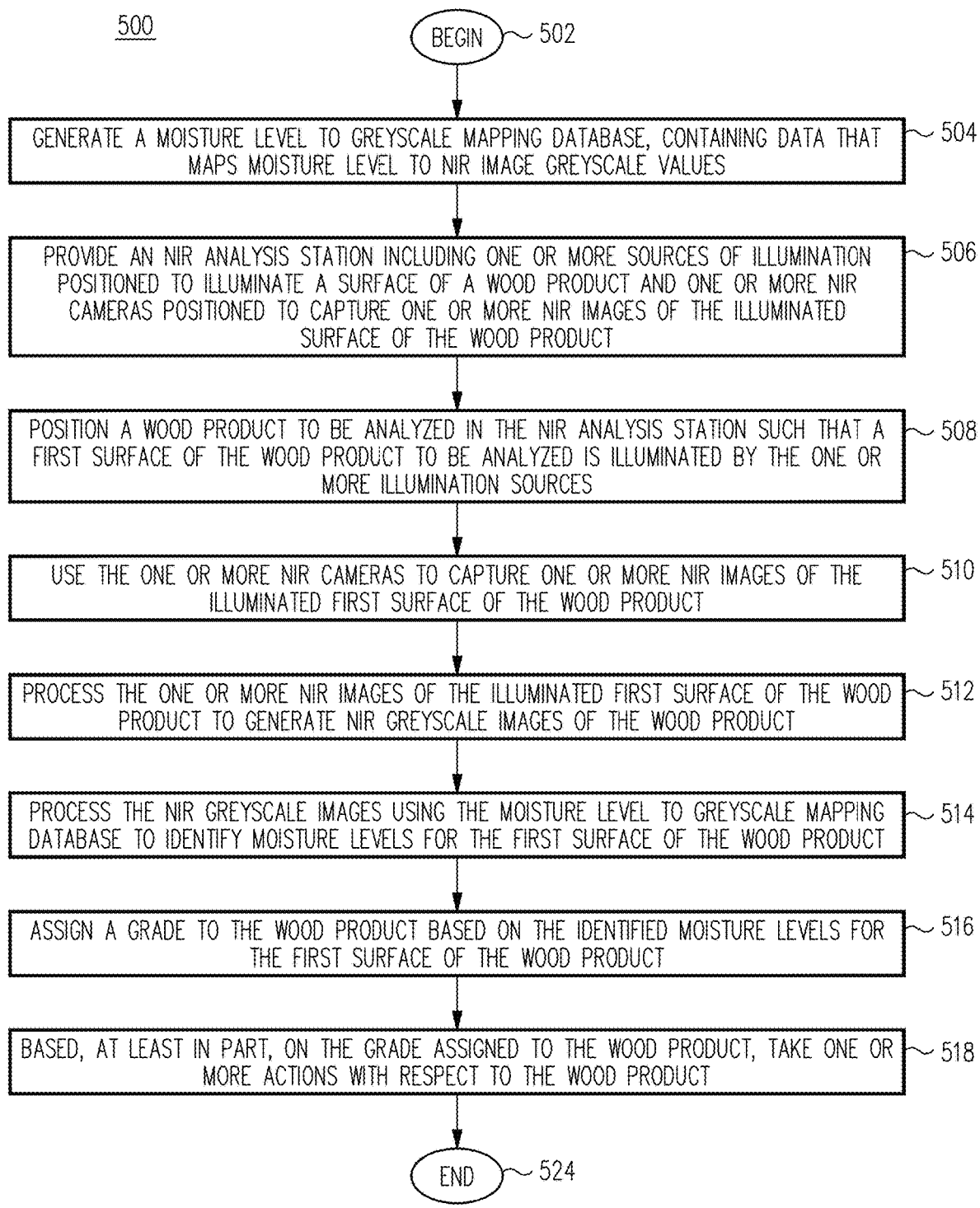
FIG. 5 is flow chart of a process for detecting moisture levels in a wood product using NIR technology in accordance with one embodiment.

FIG. 5 is flow chart of a process 500 for detecting moisture levels in a wood product using NIR technology in accordance with one embodiment.

As seen in FIG. 5, process 500 begins at BEGIN operation 502 and then process proceeds to operation 504. In one embodiment, at operation 504 a moisture level to greyscale mapping database is generated such as any database discussed above with respect to FIGS. 3A and 3B. In one embodiment, the moisture level to greyscale mapping database contains mapping data that maps moisture level to Near InfraRed (NIR) image greyscale values for one or more wood products.

In one embodiment, the mapping data is obtained through one or more empirical and/or manual processes. In one embodiment, sample wood products as first dried in a kiln or similar environment while the weight of the sample wood product is monitored. As the sample wood product dries, i.e., loses moisture, the weight of the sample wood product deceases. Once the weight of the wood product stabilizes for a defined period, such as 24 hours, the sample wood product is determined to contain minimal moisture.

Then the sample wood product is brought up in moisture content in defined increments, such as one percent of the dry sample wood product weight. At each increment, an NIR image of the sample wood product is taken and the greyscale value at that increment of moisture is determined. The greyscale value determined is then correlated to the specific moisture level at that increment.

This process is continued for multiple increments until a maximum moisture content is obtained and greyscale data for each increment is determined and correlated to the respective moisture content increment. In this way, mapping data 312 mapping each specific moisture content to a specific greyscale value is generated for the sample wood product. The process can then be repeated for different wood products, different types of wood, and under varying parameters and conditions.

Once a moisture level to greyscale mapping database is generated at operation 504, process flow proceeds to operation 506. At operation 506, an NIR analysis station is provided. In one embodiment, the NIR analysis station is substantially similar to any NIR analysis station discussed above with respect to FIGS. 3A and 3B. As discussed above, in one embodiment, the NIR analysis station includes one or more sources of illumination positioned to illuminate a surface of a wood product and one or more NIR cameras positioned to capture one or more NIR images of the illuminated surface of the wood product.

Once an NIR analysis station is provided at operation 506, process flow proceeds to operation 508. In one embodiment, at operation 508, a wood product to be analyzed is positioned in the NIR analysis station of operation 506 such that a first surface of the wood product to be analyzed is illuminated by the one or more illumination sources using any of the methods and systems discussed above with respect to FIGS. 3A and 3B.

Once the wood product to be analyzed is positioned in the NIR analysis station at 508, process flow proceeds to operation 510. In one embodiment, at operation 510 the one or more NIR cameras of NIR analysis station take one or more NIR images of the illuminated first surface of the wood product using any of the methods and systems discussed above with respect to FIGS. 3A and 3B.

Once the one or more NIR cameras of NIR analysis station take one or more NIR images of the illuminated first surface of the wood product at operation 510, process flow proceeds to operation 512.

In one embodiment, at operation 512, the one or more NIR images of the illuminated first surface of the wood product of operation 510 are processed using any of the methods and systems discussed above with respect to FIGS. 3A and 3B, to generate NIR greyscale images indicating different moisture levels in the illuminated first surface of the wood product.

Once the one or more NIR images of the illuminated first surface of the wood product are processed to generate NIR greyscale images indicating different moisture levels in the illuminated first surface of the wood product at operation 512, process flow proceeds to operation 514.

In one embodiment, at operation 514, the NIR greyscale images are processed using the moisture level to greyscale mapping database to identify moisture levels for the first surface of the wood product by any of the methods and systems discussed above with respect to FIGS. 3A and 3B.

Once the NIR greyscale images are processed using the moisture level to greyscale mapping database to identify moisture levels for the first surface of the wood product at operation 514, process flow proceeds operation 516.

In one embodiment, at operation 516 a grade is assigned to the wood product based on the identified moisture levels for the first surface of the wood product using any of the methods and systems discussed above with respect to FIGS. 3A and 3B.

Once a grade is assigned to the wood product based on the identified moisture levels for the first surface of the wood product at operation 516, process flow proceeds to operation 518. In one embodiment, at operation 518, based, at least in part, on the grade assigned to the wood product, one or more actions are taken with respect to the wood product including any of the actions discussed above with respect to the methods and systems discussed above with respect to FIGS. 3A and 3B.

Once one or more actions with respect to the wood product at operation 518, process flow proceeds to END operation 524 where process 500 is exited to await new samples and/or data.

In some embodiments, one or more visual cameras are implemented along with the one or more NIR camera to provide the capability to generate superimposed image data representing a visual/NIR composite image of wood product and correlating moisture levels with physical features of the surfaces of the wood product.

Figure 6:
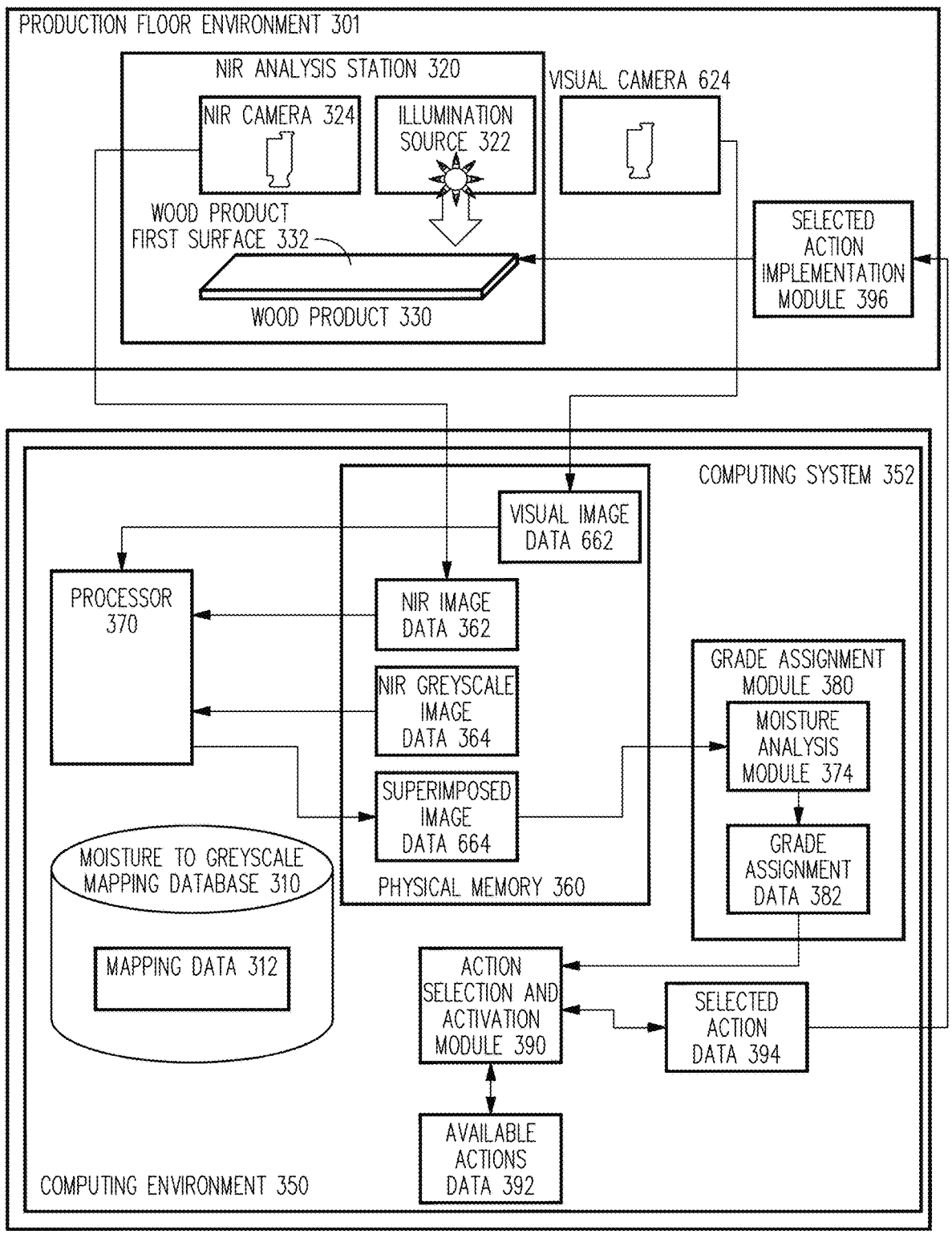
FIG. 6 is simplified block diagram of a system for detecting moisture levels in a wood product using NIR technology and visual data in accordance with one embodiment.

FIG. 6 is simplified block diagram of one embodiment of a system 600 for detecting moisture levels in a wood product using NIR technology and visual data in accordance with one embodiment.

In one embodiment, system 600 for detecting moisture levels in wood products, like system 300 of FIG. 3A and FIG. 3B, includes a production environment 301 and a computing environment 350.

As seen in FIG. 6, as in system 300 of FIG. 3A and FIG. 3B, production environment 301 includes NIR analysis station 320 and selected action implementation module 396. As seen in FIG. 6, like system 300 of FIG. 3A and FIG. 3B, NIR analysis station 320 includes one or more illumination sources, such as illumination source 322, positioned to illuminate a wood product first surface 332 of a wood product 330. In various embodiments, the one or more sources of illumination can include one or more LED light sources. In other embodiments, the one or more illumination sources, such as illumination source 322, can include, but are not limited to, halogen or halogen and tungsten light sources, or any other light sources, as discussed herein, and/or as known in the art at the time of filing, and/or as developed after the time of filing.

As seen in FIG. 6, like system 300 of FIG. 3A and FIG. 3B, NIR analysis station 320 also includes one or more NIR cameras, such as NIR camera 324, positioned to capture NIR image data 362 representing one or more NIR images of the illuminated wood product first surface 332 of the wood product 330. In one embodiment, one or more NIR cameras, such as NIR camera 324, are adjustably positioned and adjustably focused to capture one or more NIR images of the illuminated wood product first surface 332 of the wood product 330.

However, unlike like system 300 of FIG. 3A and FIG. 3B, system 600 includes one or more visual cameras, such as visual camera 624, used to take visual images of wood product first surface 332 of wood product 330 and generate visual image data 662.

As discussed in more detail below, the combination of visual image data 662 and NIR image data 362 allows for the generation of superimposed image data 664 representing a visual/NIR composite image of wood product first surface 332 of wood product 330. The visual/NIR composite image of wood product first surface 332 of wood product 330 indicates not only the presence and location of moisture, as was done using system 300, but also the location of any physical features in wood product first surface 332 of wood product 330 and the physical proximity of these features to the moisture detected in wood product first surface 332 of wood product 330.

This can be an important capability because, as explained above, it is trapped pockets of moisture that, when heated, become vapor and cause the bulges and/or damage to the wood product structure as the vapor tires to expand and escape. However, if the detected moisture is physical proximate to an open physical feature, such as a knot, knot hole, or side of the wood product, then the open physical feature provides the vapor an avenue for escape without causing damage to wood product.

Consequently, by analyzing the visual/NIR composite image represented by superimposed image data 664, moisture pockets near an open physical feature that, absent the presence open physical feature would be a problem, can be identified and ignored.

As seen in FIG. 6, and as discussed below, a wood product 330 to be analyzed in the NIR analysis station 320 is positioned in NIR analysis station 320. In various embodiments, the wood product 330 can be any wood product as discussed herein, and/or as known in the art at the time of filing and/or as becomes known after the time of filing. In one embodiment, the wood product 330 to be analyzed is a veneer sheet.

In one embodiment, the wood product 330 to be analyzed is positioned such that a wood product first surface 332 of the wood product 330 to be analyzed is illuminated by the illumination source 322 and is within view and focus of NIR camera 324 and visual camera 624. In one embodiment, the wood product 330 is positioned in the NIR analysis station 320 by passing the wood product through the NIR analysis station 320 on a conveyor system (not shown in FIG. 6 but shown as 321 in FIG. 3B and discussed above).

As seen in FIG. 6, computing environment 350 includes computing system 352. As seen in FIG. 6, as with system 300 of FIGS. 3A and 3B, in one embodiment, computing system 352 includes moisture to greyscale mapping database 310 containing mapping data 312 that maps moisture level to Near InfraRed (NIR) image greyscale values for one or more wood products.

As seen in FIG. 6, as with system 300 of FIGS. 3A and 3B, computing system 352 includes physical memory 360. For use with system 600, physical memory 360 includes NIR image data 362 representing one or more NIR images of the illuminated wood product first surface 332 of the wood product 330 captured using NIR camera 324, visual image data 662 representing one or more visual images of the illuminated wood product first surface 332 of the wood product 330 captured using visual camera 624, and superimposed image data 664 representing a visual/NIR composite image of wood product first surface 332 of wood product 330, as discussed above.

As seen in FIG. 6, in one embodiment, computing system 352 includes one or more processors 370 for processing the NIR image data 362 representing one or more NIR images of the illuminated wood product first surface 332 of the wood product 330 to generate NIR greyscale image data 364 indicating different moisture levels in the illuminated wood product first surface 332 of the wood product 330.

In one embodiment, processor 370 processes the NIR greyscale image data 364 using the mapping data 312 from moisture to greyscale mapping database 310 data to identify moisture levels for the wood product first surface 332 of the wood product 330.

In the specific embodiment of FIG. 6, processors 370 also process visual image data 662 and NIR greyscale image data 364 to generate superimposed image data 664 representing a visual/NIR composite image of wood product first surface 332 of wood product 330, as discussed above.

Figure 7A:
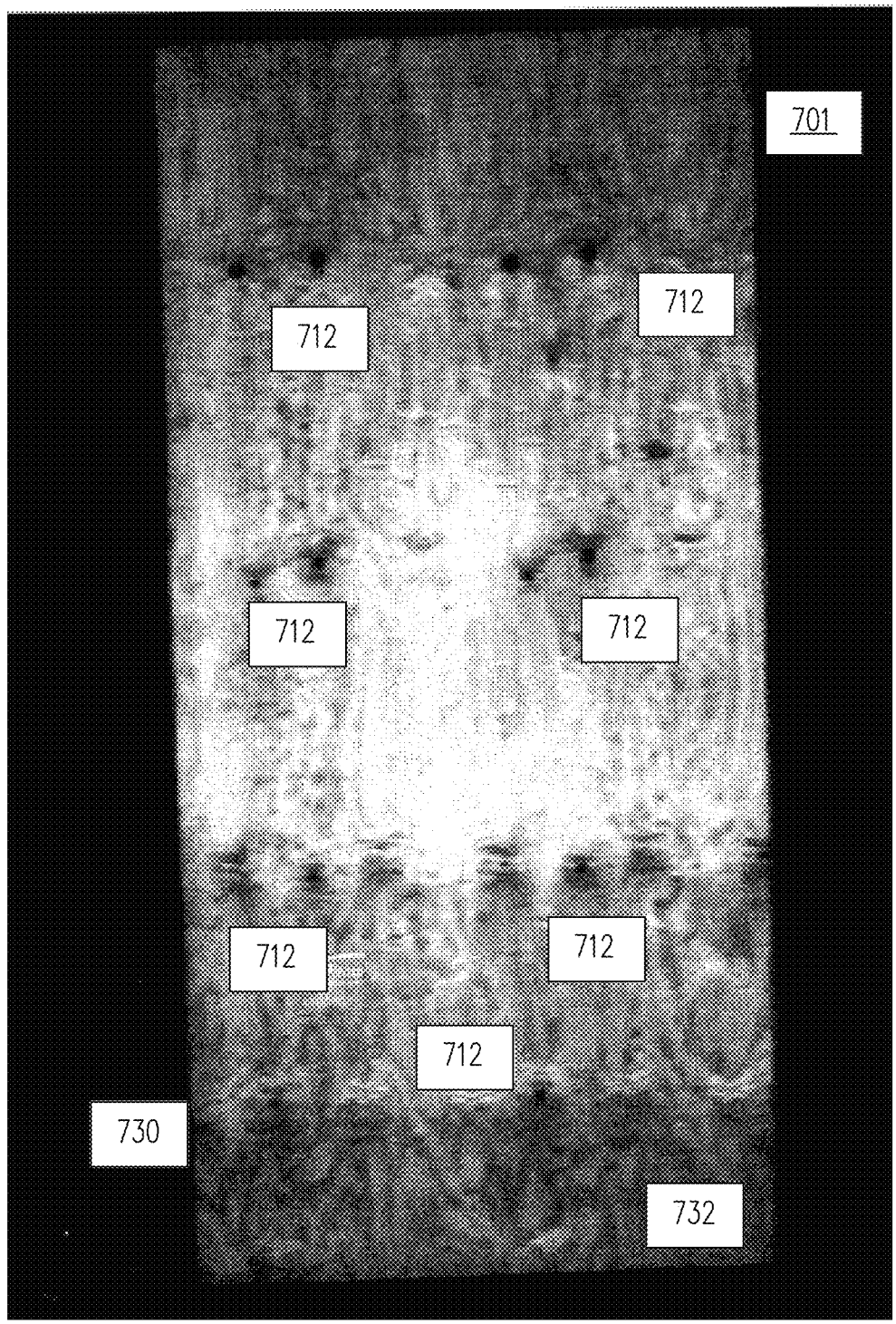
FIG. 7A shows a black and white visual image of a wood product first surface of a veneer sheet including physical features which, in this specific illustrative example, are knots and knot holes.

FIG. 7A shows a black and white visual image 701 of a wood product first surface 732 of a veneer sheet 730. As seen in FIG. 7A, wood product first surface 732 includes physical features 712 which, in this specific illustrative example, are knots and knot holes.

Figure 7B:
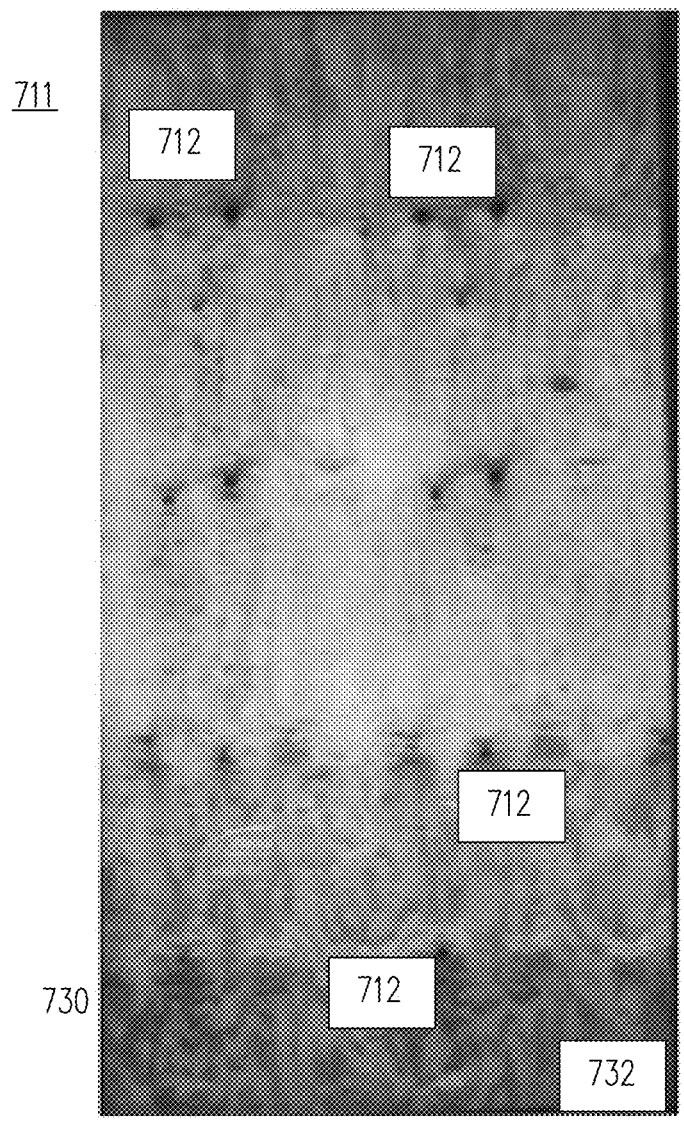
FIG. 7B shows a color visual image of the wood product first surface of the veneer sheet of FIG. 7A including physical features which, in this specific illustrative example, are knots and knot holes of FIG. 7A.

FIG. 7B shows a color visual image 711 of wood product first surface 732 of veneer sheet 730, including physical features 712 which, as noted, in this specific illustrative example, are knots and knot holes.

Figure 7C:
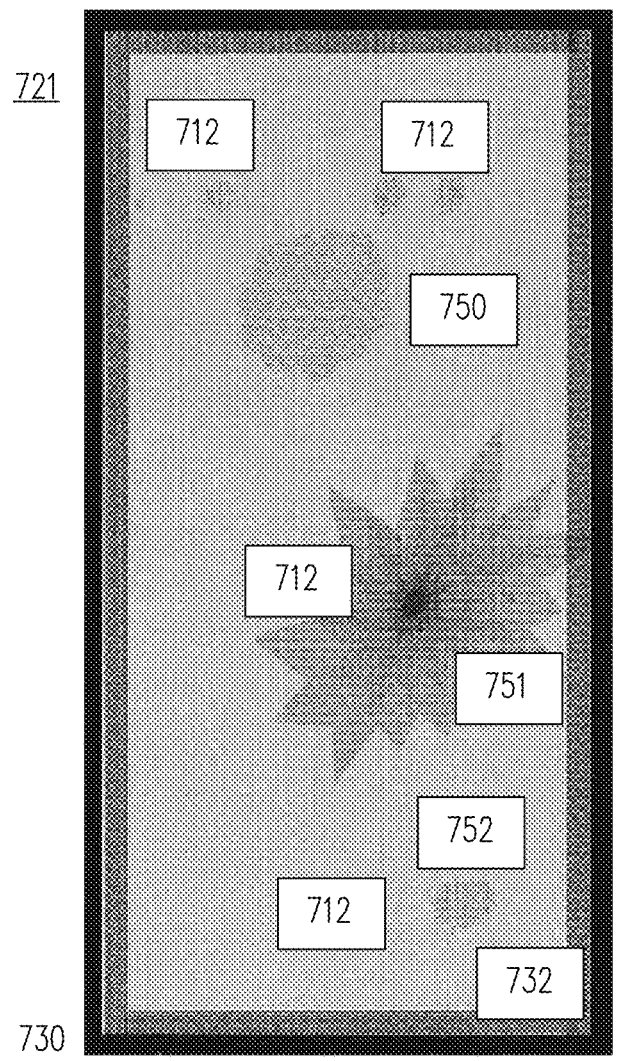
FIG. 7C shows a superimposed composite image of the wood product first surface the of the wood product including the visual images of the physical features of FIG. 7A or 7B with an NIR greyscale image including NIR greyscale images of high moisture superimposed.

FIG. 7C shows a superimposed composite image 721 of the wood product first surface 732 of the wood product 730. As seen in FIG. 7C, superimposed composite image 721 includes the visual images of physical features 712 of either black and white visual image 701 or color visual image 711. However, superimposed on these visual images is a NIR greyscale image including NIR greyscale images of high moisture pockets 750, 751, and 752.

The superimposed composite image 721 not only shows the areas of high moisture, i.e., high moisture pockets 750, 751, and 752, but also their proximity to physical features 712 which, in this specific illustrative example, are knots and knot holes. By analyzing the superimposed composite image 721, moisture pockets near an open physical feature, such as high moisture pockets 750 and 752 that, absent the presence open physical features/knots 712, would be a problem can be identified and ignored.

Figure 7D:
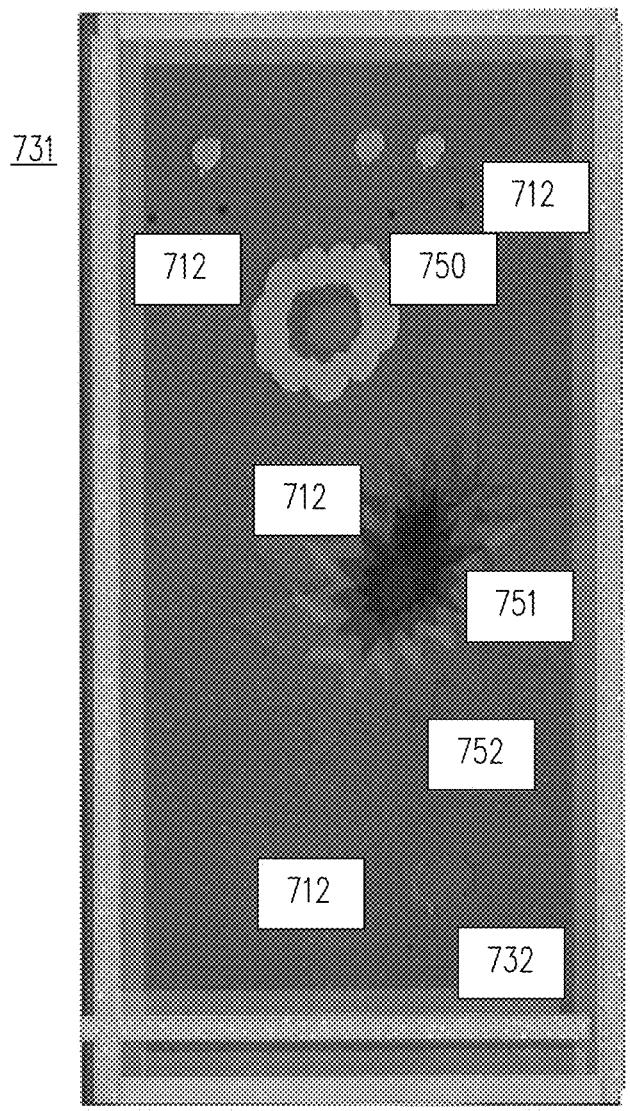
FIG. 7D shows a color enhanced superimposed composite image of the wood product first surface the of the wood product of FIG. 7C.

FIG. 7D shows a color enhanced superimposed composite image 731 that is created using a greyscale to color mapping database to provide even more pronounced visualization of the high moisture pockets 750, 751, and 752.

It is worth noting again that visual images 701, 711, 721, and 731 can be images of the entire wood product first surface 732 of veneer sheet 730, i.e., can be a 4'×8' sample.

In addition, as noted above, using a standard 1.3 mega pixel camera to obtain images 701, 711, 721, and 731 of the entire wood product first surface 732 of veneer sheet 730 there are as many as 1,300,000 data points, i.e., each pixel is a data point. This, in turn, gives rise to very high resolution and is in sharp contrast to the 128 9"×3" samples of traditional contact electrode systems or 32 12"×12" samples of traditional RF systems that, as discussed above, yielded ±5.0% or ±7.5% margins of error, respectively.

As seen in FIG. 6, in one embodiment, computing system 352 includes a grade assignment module 380 for assigning a grade to the wood product 330 based on the identified moisture levels and visual data of superimposed image data 664 for the wood product first surface 332. As seen in FIG. 3A, grade assignment module 380 includes moisture analysis module 374 which, along with processor 370, processes superimposed image data 664 for the wood product first surface 332 to identify moisture levels and open features for the wood product first surface 332 of the wood product 330. As a result of the processing by moisture analysis module 374 and processor 370, grade assignment data 382 is generated.

As seen in FIG. 6, in one embodiment, grade assignment data 382 is provided to action selection and activation module 390 which selects an appropriate action of the actions represented in available actions data 392 based, at least in part on the grade indicated by grade assignment data 382. As seen in FIG. 6, in one embodiment, the determined appropriate action is represented by selected action data 394.

As seen in FIG. 6, in one embodiment, selected action data 394 is forwarded to an action activation module such as selected action implementation module 396 in production environment 301 to initialize one or more actions with respect to the wood product 330 based, at least in part, on the grade represented by grade assignment data 382 and assigned to the wood product 330 by action selection and activation module 390.

In one embodiment, one or more actions that can be taken represented in available actions data 392 include, but are not limited to: sorting the wood product 330 into a bin or location associated with the grade represented by grade assignment data 382 and assigned to the wood product 330; restricting the use of the wood product 330 based on the grade represented by grade assignment data 382 and assigned to the wood product 330; rejecting the wood product 330 based on the grade represented by grade assignment data 382 and assigned to the wood product 330; sending the wood product 330 back for further processing based on the grade represented by grade assignment data 382 and assigned to the wood product 330; adjusting one or more processing parameters of a production line in production environment 301 based, at least in part, on the grade represented by grade assignment data 382 and assigned to the wood product 330 and/or the grades assigned other wood products; adjusting drying temperatures on a production line in production environment 301 based, at least in part, on grade represented by grade assignment data 382 and assigned to the wood product 330 and/or the grades assigned other wood products; adjusting drying times on a production line in production environment 301 based, at least in part, on grade represented by grade assignment data 382 and assigned to the wood product 330 and/or the grades assigned other wood products; and; and selecting a type and amounts of glues used on a production line in production environment 301 based, at least in part, on grade represented by grade assignment data 382 and assigned to the wood product 330 and/or the grades assigned other wood products.

Those of skill in the art will ready recognize that the specific illustrative examples of embodiments of FIGS. 6, 7A, 7B, 7C, and 7D are but specific example of numerous possible production environments, arrangement of components, and images. Consequently, the specific illustrative examples of embodiments of FIGS. 6, 7A, 7B, 7C, and 7D are not intended to limit the scope of the invention as set forth in the claims below.

As a specific illustrative example of potential variations, in various embodiments, the NIR analysis station 320 can include one or more illumination sources 322 positioned to illuminate two or more surfaces of a wood product and one or more NIR cameras 324 positioned to capture one or more NIR images of the two or more illuminated surfaces of the wood product. In one embodiment, one or visual cameras 624 can be positioned to capture one or more NIR images of the two or more illuminated surfaces of the wood product.

Figure 8:
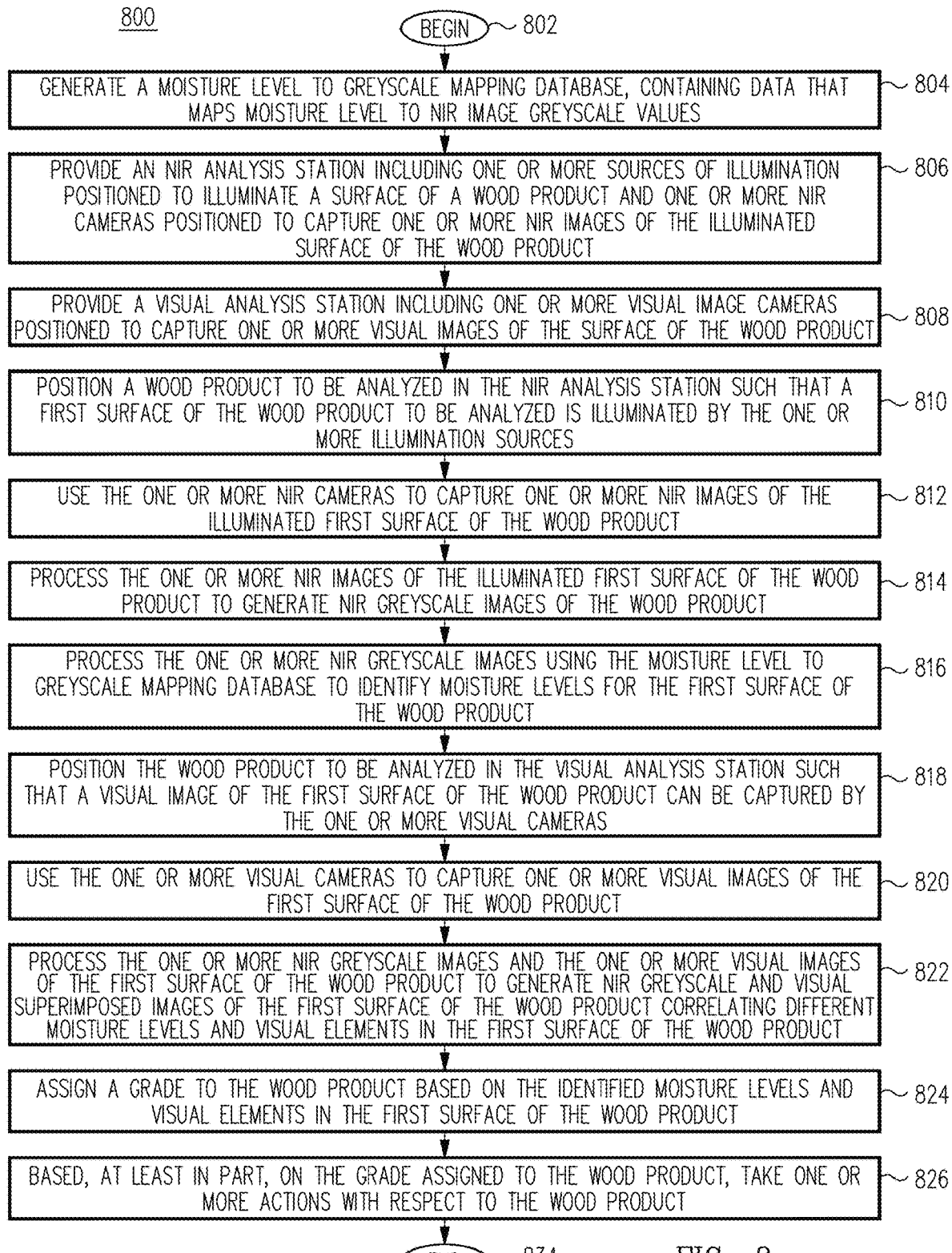
FIG. 8 is flow chart of a process for detecting moisture levels in a wood product using NIR technology and visual data in accordance with one embodiment.

FIG. 8 is flow chart of a process 800 for detecting moisture levels in a wood product using NIR technology and visual data in accordance with one embodiment.

As seen in FIG. 8, process 800 begins at BEGIN operation 802 and then process proceeds to operation 804. In one embodiment, at operation 804 a moisture level to greyscale mapping database is generated such as any database discussed above with respect to FIGS. 3A, 3B and 6. In one embodiment, the moisture level to greyscale mapping database contains mapping data that maps moisture level to Near InfraRed (NIR) image greyscale values for one or more wood products.

Once a moisture level to greyscale mapping database is generated at operation 804, process flow proceeds to operation 806. At operation 806, an NIR analysis station is provided. In one embodiment, the NIR analysis station is substantially similar to any NIR analysis station discussed above with respect to FIGS. 3A, 3B, and 6. As discussed above, in one embodiment, the NIR analysis station includes one or more sources of illumination positioned to illuminate a surface of a wood product and one or more NIR cameras positioned to capture one or more NIR images of the illuminated surface of the wood product.

Returning to FIG. 8, once an NIR analysis station is provided at operation 806, process flow proceeds to operation 808. In one embodiment, at operation 808 a visual analysis station is provided including one or more visual image cameras such as any visual cameras discussed above with respect to FIG. 6. In one embodiment, one or more visual image cameras are adjustably positioned to capture visual images of the first surface of the wood product using any method or system as discussed above with respect to FIGS. 3A, 3B, and 6.

In one embodiment, once one or more visual image cameras are provided at operation 808, process flow proceeds to operation 810. In one embodiment, at operation 810, a wood product to be analyzed is positioned in the NIR analysis station of operation 806 such that a first surface of the wood product to be analyzed is illuminated by the one or more illumination sources using any of the methods and systems discussed above with respect to FIGS. 3A, 3B and 6.

Once the wood product to be analyzed is positioned in the NIR analysis station at operation 810, process flow proceeds to operation 812. In one embodiment, at operation 812 the one or more NIR cameras of NIR analysis station take one or more NIR images of the illuminated first surface of the wood product using any of the methods and systems discussed above with respect to FIGS. 3A, 3B and 6.

Once the one or more NIR cameras of NIR analysis station take one or more NIR images of the illuminated first surface of the wood product at operation 812, process flow proceeds to operation 814.

In one embodiment, at operation 814, the one or more NIR images of the illuminated first surface of the wood product of operation 812 are processed using any of the methods and systems discussed above with respect to FIGS. 3A, 3B and 6, to generate NIR greyscale images indicating different moisture levels in the illuminated first surface of the wood product.

Once the one or more NIR images of the illuminated first surface of the wood product are processed to generate NIR greyscale images indicating different moisture levels in the illuminated first surface of the wood product at operation 814, process flow proceeds to operation 816.

In one embodiment, at operation 816, the NIR greyscale images are processed using the moisture level to greyscale mapping database to identify moisture levels for the first surface of the wood product by using any of the methods and systems discussed above with respect to FIGS. 3A, 3B and 6.

Once the NIR greyscale images are processed using the moisture level to greyscale mapping database to identify moisture levels for the first surface of the wood product at operation 816, process flow proceeds operation 818.

In one embodiment, at operation 818, the wood product is positioned in the visual analysis station of operation 808 such that one or more visual images of the first surface of the wood product can be captured using the one or more visual image cameras of operation 808 and using any of the methods and systems discussed above with respect to FIGS. 3A, 3B and 6.

Once the wood product is positioned such that one or more visual images of the first surface of the wood product can be captured at operation 818, process flow proceeds to operation 820. In one embodiment at operation 820 one or more visual images of the first surface of the wood product are captured using the one or more visual image cameras of operation 808 and using any of the methods and systems discussed above with respect to FIGS. 3A, 3B and 6.

Once one or more visual images of the first surface of the wood product are captured at operation 820, process flow proceeds to operation 822. In one embodiment, at operation 822 the one or more NIR greyscale images and the one or more visual images of the first surface of the wood product are processed to generate NIR greyscale and visual superimposed images of the first surface of the wood product correlating different moisture levels and visual elements in the first surface of the wood product using any of the methods and systems discussed above with respect to FIGS. 3A, 3B and 6.

As noted above, the combination of visual image data and NIR image data allows for the generation of superimposed image data and a visual/NIR composite image of the wood product first surface. The visual/NIR composite image of the wood product first surface indicates not only the presence and location of moisture, as was done using process 500, but also the location of any physical features in wood product first surface of the wood product and the physical proximity of these features to the moisture detected in wood product first surface.

This can be critical feature because, as explained above, it is trapped pockets of moisture that, when heated, become vapor and cause the bulges and/or damage to the wood product structure as the vapor tires to expand and escape. However, if the detected moisture is physical proximate to open physical feature, such as a knot, knot hole, or side of the wood product, then the open physical feature provides the vapor an avenue for escape without causing damage to wood product.

Consequently, by analyzing the visual/NIR composite image represented by superimposed image data of operation 822 at operation 824 discussed below, moisture pockets near an open physical feature that, absent the presence open physical feature would be an issue, can be identified and ignored.

Once the one or more NIR greyscale images and the one or more visual images of the first surface of the wood product are processed to generate NIR greyscale and visual superimposed images of the first surface of the wood product correlating different moisture levels and visual elements in the first surface of the wood product at operation 822, process flow proceeds to operation 824.

In one embodiment, at operation 824 a grade is assigned to the wood product based on the identified moisture levels and visual elements in the first surface of the wood product using any of the methods and systems discussed above with respect to FIGS. 3A, 3B and 6.

Once a grade is assigned to the wood product based on the identified moisture levels and visual elements in the first surface of the wood product at operation 824, process flow proceeds to operation 826. In one embodiment, at operation 826, based, at least in part, on the grade assigned to the wood product, taking one or more actions with respect to the wood product including any of the actions discussed above with respect to the methods and systems discussed above with respect to FIGS. 3A, 3B and 6.

Once one or more actions with respect to the wood product at operation 818, process flow proceeds to END operation 834 where process 800 is exited to await new samples and/or data.

In some embodiments, machine leaning based models are used to predict moisture levels and behavior of wood products based on NIR image data for a wood product under analysis.

Figure 9:
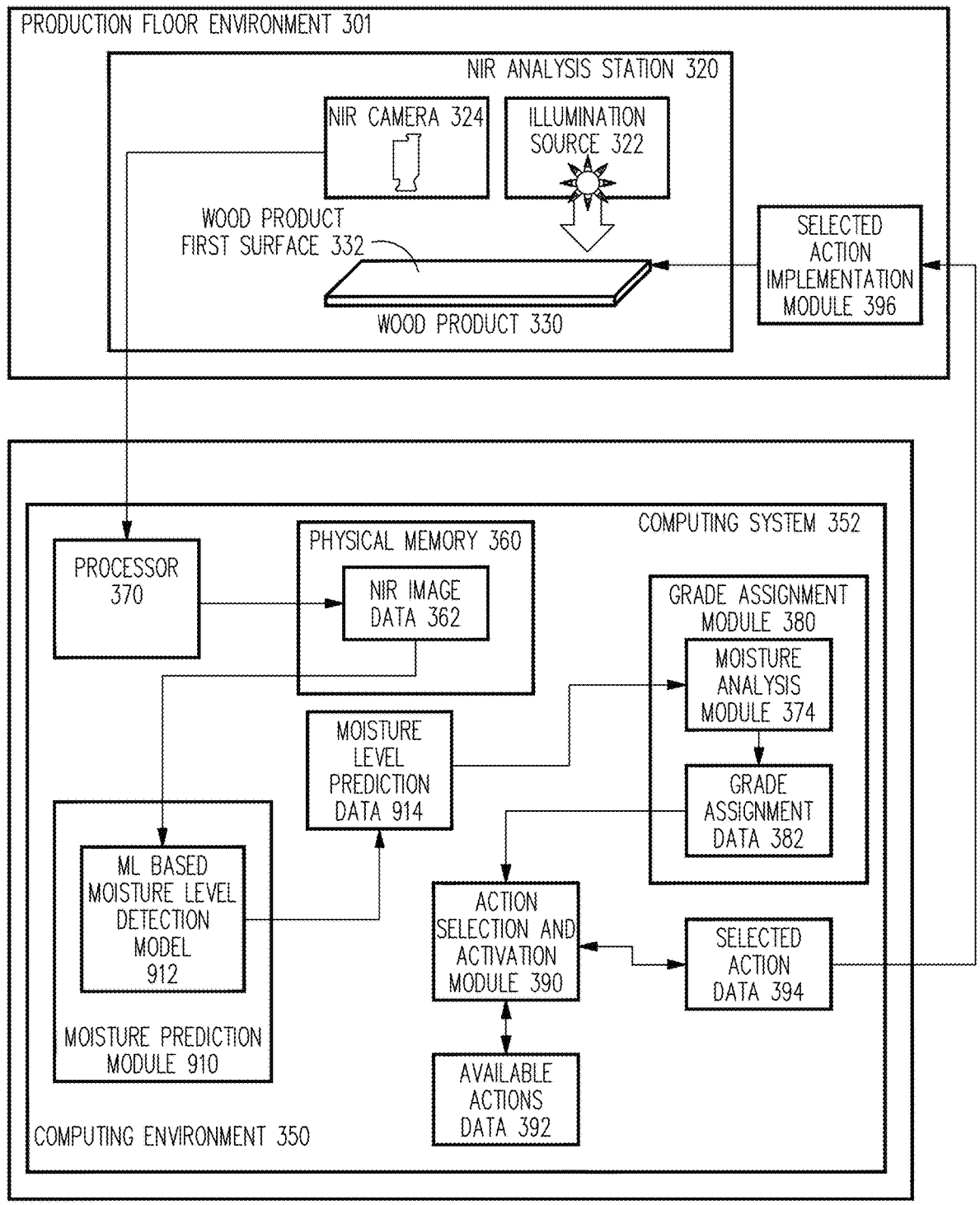
FIG. 9 is simplified block diagram of a system for detecting moisture levels in a wood product using NIR technology and machine learning methods in accordance with one embodiment.

FIG. 9 is simplified block diagram of one embodiment of a system 900 for detecting moisture levels in a wood product using NIR technology and machine learning methods in accordance with one embodiment.

In one embodiment, system 900 for detecting moisture levels in wood products, like system 300 of FIGS. 3A and 3B, includes production environment 301 and a computing environment 350.

As seen in FIG. 9, like system 300 of FIGS. 3A and 3B, production environment 301 includes NIR analysis station 320 and selected action implementation module 396. As seen in FIG. 9, NIR analysis station 320 includes one or more illumination sources, such as illumination source 322, positioned to illuminate a wood product first surface 332 of a wood product 330. In various embodiments, the one or more sources of illumination, such as illumination source 322, can include one or more LED light sources. In other embodiments, the one or more illumination sources, such as illumination source 322, can include, but are not limited to, halogen or halogen and tungsten light sources, or any other light sources, as discussed herein, and/or as known in the art at the time of filing, and/or as developed after the time of filing.

As seen in FIG. 9, NIR analysis station 320 also includes one or more NIR cameras, such as NIR camera 324, positioned to capture NIR image data 362 representing one or more NIR images of the illuminated wood product first surface 332 of the wood product 330. In one embodiment, one or more NIR cameras, such as NIR camera 324, are adjustably positioned and adjustably focused to capture one or more NIR images of the illuminated wood product first surface 332 of the wood product 330.

As seen in FIG. 9, and as discussed below, the wood product 330 to be analyzed in the NIR analysis station 320 is positioned in NIR analysis station 320. In various embodiments, the wood product 330 can be any wood product as discussed herein, and/or as known in the art at the time of filing and/or as becomes known after the time of filing. In one embodiment, the wood product 330 to be analyzed is a veneer sheet.

In one embodiment, the wood product 330 to be analyzed is positioned such that the wood product first surface 332 of the wood product 330 to be analyzed is illuminated by the illumination source 322 and is within view and focus of NIR camera 324. In one embodiment, the wood product 330 is positioned in the NIR analysis station 320 by passing the wood product 330 through the NIR analysis station 320 on a conveyor system (not shown in FIG. 9 but shown as 321 in FIG. 3B and discussed below).

As seen in FIG. 9, like system 300 of FIGS. 3A and 3B, computing environment 350 includes computing system 352. However, unlike system 300 of FIGS. 3A and 3B, as seen in FIG. 9, in one embodiment, computing system 352 of system 900 does not include moisture to greyscale mapping database 310 but instead includes moisture prediction module 910.

In one embodiment, moisture prediction module 910 includes one or more trained Machine Learning (ML) based moisture level detection models, such as Machine Learning (ML) based moisture detection model 912. In various embodiments the one or more trained machine learning based moisture level detection models, such as machine learning based moisture detection model 912, are trained using NIR image data for one or more wood products and corresponding determined moisture levels for the one or more wood products.

Various types of machine learning based models are well known in the art. Consequently the one or more trained machine learning based moisture level detection models, such as machine learning based moisture detection model 912, can be any machine learning based model type or use any machine learning based algorithm, as discussed herein, and/or as known in the art at the time of filing, and/or as becomes known or available after the time of filing.

Specific illustrative examples of machine learning based model types and machine learning based algorithms that can be used for, or with, the one or more trained machine learning based moisture level detection models of moisture prediction module 910, such as machine learning based moisture detection model 912, include, but are not limited to: supervised machine learning-based models; semi-supervised machine learning-based models; unsupervised machine learning-based models; classification machine learning-based models; logistical regression machine learning-based models; neural network machine learning-based models; and deep learning machine learning-based models.

In various embodiments, and largely depending on the machine-learning based models used, the NIR image data for one or more wood products, including in some cases various environmental and production parameters, and corresponding determined moisture levels for the one or more wood products can be processed using various methods known in the machine learning arts to identify elements and vectorize the NIR image data and/or corresponding determined moisture levels data. As a specific illustrative example, in a case where the machine leaning based model is a supervised model, the NIR image data can be analyzed and processed into elements found to be indicative of a wood product moisture levels and product performance. Then these elements are used to create vectors in multidimensional space which are, in turn, used as input data for one or more machine learning models. The correlated determined moisture levels data for each NIR image data vector is then used as a label for the resulting vector. This process is repeated for multiple, often millions, of correlated pairs of NIR image data vector and determined moisture levels data with the result being one or more trained machine learning based moisture level detection models.

Then when new NIR image data is obtained, this new NIR image data is also vectorized and the new NIR image vector data is provided as input data to the one or more trained machine learning based moisture level detection models. The new NIR image vector data is then processed to find a distance between the new NIR image vector and previously labeled NIR image vectors, whose associated moisture level data is known. Based on a calculated distance between the new NIR image vector data and the previously labeled NIR image vector data, a probability that the new NIR image vector data correlates to a moisture level associated with the previously labeled NIR image vector data can be calculated. This results in a probability score for the wood product being analyzed.

Those of skill in the art will readily recognize that there are many different types of machine learning based models known in the art. Consequently, the specific illustrative example of a specific supervised machine learning based model discussed above is not limiting.

As seen in FIG. 9, computing system 352 also include physical memory 360. In one embodiment, the physical memory 360 includes NIR image data 362 representing one or more NIR images of the illuminated wood product first surface 332 of the wood product 330 captured using NIR camera 324.

As seen in FIG. 9, in one embodiment, computing system 352 includes one or more processors, such as processor 370, for generating the NIR image data 362 representing one or more NIR images of the illuminated wood product first surface 332 of the wood product 330 from NIR camera 324.

In one embodiment, NIR image data 362 is provided to moisture prediction module 910 where it is processed/vectorized and provided to machine learning based moisture level detection model 912.

Machine learning based moisture level detection model 912 then processes the vectorized NIR image data 362 as discussed above and generates moisture level prediction data 914 for the wood product 330.

As seen in FIG. 9, moisture level prediction data 914 for the wood product 330 is then provided to grade assignment module 380. As discussed above, grade assignment module 380 then assigns a grade to the wood product 330 based on moisture level prediction data 914 for the wood product 330.

As seen in FIG. 9, grade assignment module 380 includes moisture analysis module 374 which, along with processor 370, processes moisture level prediction data 914 for the wood product 330 and generates grade assignment data 382 based on this processing As seen in FIG. 9, in one embodiment, grade assignment data 382 is provided to action selection and activation module 390 which selects an appropriate action of the actions represented in available actions data 392 based, at least in part on the grade indicated by grade assignment data 382. As seen in FIG. 9, in one embodiment, the determined appropriate action is represented by selected action data 394.

As seen in FIG. 9, in one embodiment, selected action data 394 is forwarded to an action activation module, such as selected action implementation module 396 in production environment 301 to initialize one or more actions with respect to the wood product 330 based, at least in part, on the grade represented by grade assignment data 382 and assigned to the wood product 330 by action selection and activation module 390.

In one embodiment, one or more actions that can be taken represented in available actions data 392 include, but are not limited to: sorting the wood product 330 into a bin or location associated with the grade represented by grade assignment data 382 and assigned to the wood product 330; restricting the use of the wood product 330 based on the grade represented by grade assignment data 382 and assigned to the wood product 330; rejecting the wood product 330 based on the grade represented by grade assignment data 382 and assigned to the wood product 330; sending the wood product 330 back for further processing based on the grade represented by grade assignment data 382 and assigned to the wood product 330; adjusting one or more processing parameters of a production line in production environment 301 based, at least in part, on the grade represented by grade assignment data 382 and assigned to the wood product 330 and/or the grades assigned other wood products; adjusting drying temperatures on a production line in production environment 301 based, at least in part, on grade represented by grade assignment data 382 and assigned to the wood product 330 and/or the grades assigned other wood products; adjusting drying times on a production line in production environment 301 based, at least in part, on grade represented by grade assignment data 382 and assigned to the wood product 330 and/or the grades assigned other wood products; and selecting a type and amount of glues used on a production line in production environment 301 based, at least in part, on grade represented by grade assignment data 382 and assigned to the wood product 330 and/or the grades assigned other wood products.

Those of skill in the art will ready recognize that the specific illustrative example of one embodiment of FIG. 9 is but one example of numerous possible production environments and arrangement of components. Consequently, the specific illustrative example of one embodiment shown in FIG. 9 is not intended to limit the scope of the invention as set forth in the claims below.

As a specific illustrative example of possible variations, in some embodiments, the NIR analysis station 320 can include one or more illumination sources 322 positioned to illuminate two or more surfaces of a wood product and one or more NIR cameras 324 positioned to capture one or more NIR images of the two or more illuminated surfaces of the wood product.

Figure 10:
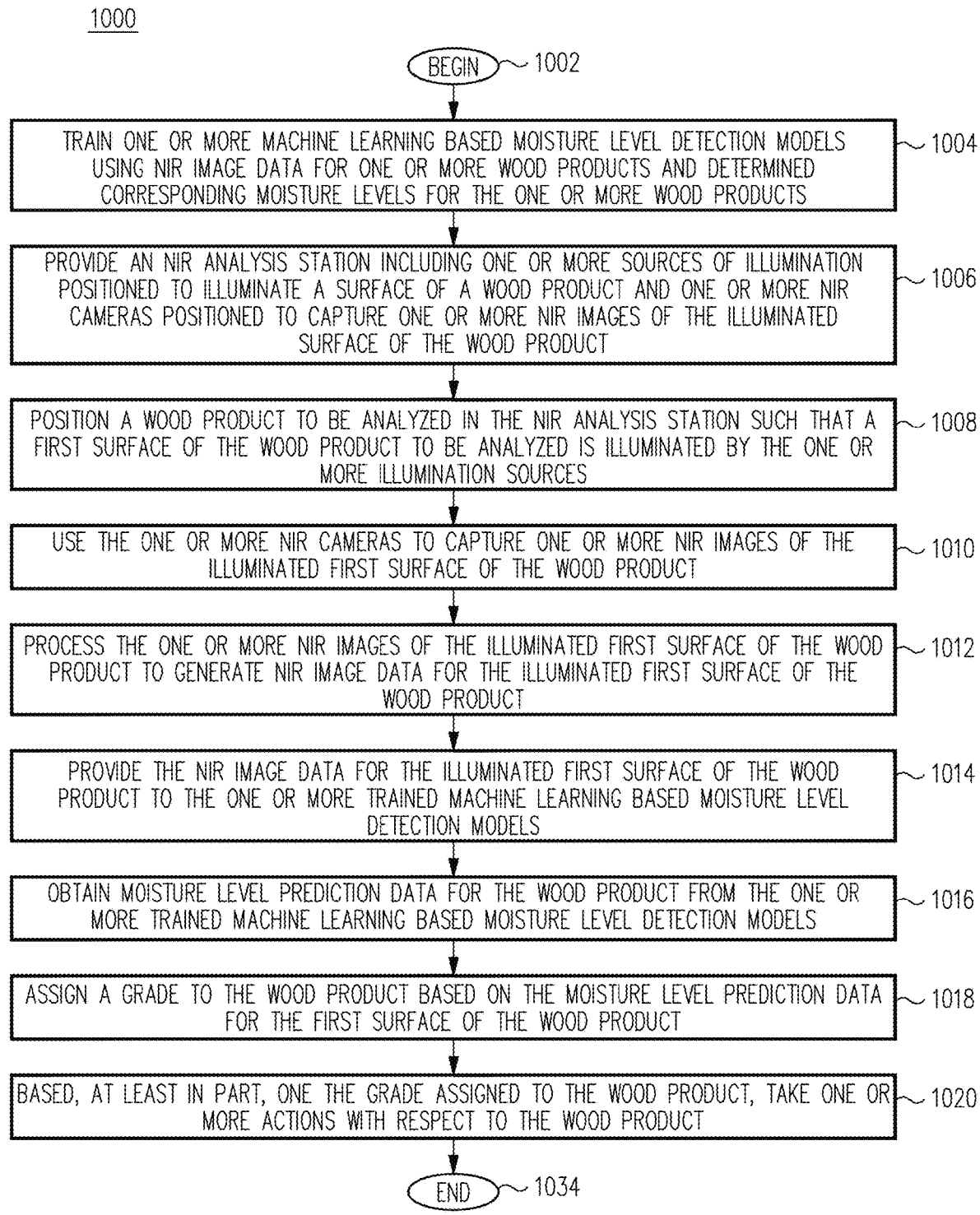
FIG. 10 is flow chart of a process for detecting moisture levels in a wood product using NIR technology and machine learning methods in accordance with one embodiment.

FIG. 10 is flow chart of a process 1000 for detecting moisture levels in a wood product using NIR technology and machine learning methods in accordance with one embodiment.

As seen in FIG. 10, process 1000 begins at BEGIN operation 1002 and then process proceeds to operation 1004. In one embodiment, at operation 1004 one or more machine learning based moisture level detection models are trained using NIR image data for one or more wood products and determined corresponding moisture levels for the one or more wood products by any of the systems or methods discussed above with respect to FIG. 9.

In one embodiment, once one or more machine learning based moisture level detection models are trained using NIR image data for one or more wood products and determined corresponding moisture levels for the one or more wood products at operation 1004, process flow proceeds to operation 1006.

At operation 1006, an NIR analysis station is provided. In one embodiment, the NIR analysis station is substantially similar to any NIR analysis station discussed above with respect to FIGS. 3A, 3B and 9. As discussed above, in one embodiment, the NIR analysis station includes one or more sources of illumination positioned to illuminate a surface of a wood product and one or more NIR cameras positioned to capture one or more NIR images of the illuminated surface of the wood product.

Once an NIR analysis station is provided at operation 1006, process flow proceeds to operation 1008. In one embodiment, at operation 1008, a wood product to be analyzed is positioned in the NIR analysis station of operation 1006 such that a first surface of the wood product to be analyzed is illuminated by the one or more illumination sources using any of the methods and systems discussed above with respect to FIGS. 3A, 3B and 9.

Once the wood product to be analyzed is positioned in the NIR analysis station at 1008, process flow proceeds to operation 1010. In one embodiment, at operation 1010 the one or more NIR cameras of NIR analysis station take one or more NIR images of the illuminated first surface of the wood product using any of the methods and systems discussed above with respect to FIGS. 3A, 3B and 9.

Once the one or more NIR cameras of NIR analysis station take one or more NIR images of the illuminated first surface of the wood product at operation 1010, process flow proceeds to operation 1012.

In one embodiment, at operation 1012, the one or more NIR images of the illuminated first surface of the wood product of operation 1010 are processed, using any of the methods and systems discussed above with respect to 9, to generate NIR images data such as any NIR image data discussed above with respect to FIGS. 3A, 3B and 9.

Once the one or more NIR images of the illuminated first surface of the wood product are processed to generate NIR images data at operation 1012, process flow proceeds to operation 1014.

In one embodiment, at operation 1014 the NIR image data for the illuminated first surface of the wood product of operation 1012 is processed and provided to the one or more trained machine learning based moisture level detection models using any of the methods and systems discussed above with respect to FIG. 9.

Once the NIR image data for the illuminated first surface of the wood product is processed and provided to the one or more trained machine learning based moisture level detection models at operation 1014, process flow proceeds to process 1016.

In one embodiment, at operation 1016 one or more trained machine learning based moisture level detection models generate moisture level prediction data for the wood product using any of the methods and systems discussed above with respect to FIG. 9.

Once moisture level prediction data for the wood product is obtained from the one or more trained machine learning based moisture level detection models at operation 1016, process flow proceeds to operation 1018.

In one embodiment, at operation 1018, a grade is assigned to the wood product based on the based on the moisture level prediction data for the wood product at operation 1016 using any of the methods and systems discussed above with respect to FIG. 9.

Once a grade is assigned to the wood product based on the based on the moisture level prediction data for the wood product at operation 1018, process flow proceeds to operation 1020. In one embodiment, at operation 1020, based, at least in part, on the grade assigned to the wood product, one or more actions are taken with respect to the wood product including any of the actions discussed above with respect to the methods and systems discussed above with respect to FIGS. 3A, 3B and 9.

Once one or more actions with respect to the wood product at operation 1020, process flow proceeds to END operation 1034 where process 1000 is exited to await new samples and/or data.

As shown above, the disclosed embodiments utilize NIR cameras to scan the surface of a wood product for moisture and create an NIR image of the surface of the wood product. Since essentially each pixel of camera image data is a sample point, the resolution and accuracy of the moisture detection process is the number of pixels the camera has covering the field of view, e.g., the entire first surface of a wood product. Consequently, in the case where a 1.3 mega pixel camera is there are essential 1,300,000 individual measurement points on the surface of the wood product. Consequently, using NIR cameras, as disclosed herein, results in resolutions and accuracy that simply cannot be achieved using traditional moisture detection systems such as traditional contact electrode systems or RF moisture detection systems.

As noted, using traditional moisture detection systems such as traditional contact electrode systems or RF moisture detection systems accuracy levels are at best subject to the ±5% or the ±7.5% margin of error, respectively. This resulted in the need to be very conservative when determining the potential use of a given veneer sheet or other wood product and often resulted in wood products, such as veneer sheets, not being put to their most cost effective and efficient use simply to ensure that the ±5% or the ±7.5% margin of error did not result in inferior or unsafe wood products.

In contrast, using the disclosed NIR-based systems, accuracy on the order of ±0.1% is readily achieved. Therefore, the highest value use of a given veneer sheet or other wood product can be accurately determined and the wood products, such as veneer sheets, can be confidently put to their most cost effective and efficient use.

In addition, when, as disclosed herein, NIR cameras are used as the moisture detection mechanism, when greater or less resolution is deemed necessary, a higher or lower mega-pixel camera can be selected to achieve the desired resolution for the process. In addition, unlike tradition contact electrode and RF moisture detection systems, NIR camera placement with respect to the sample under analysis can be adjusted such that a quality image can be obtained as long as there is a clear field of view between the wood product surface and NIR camera. Horizontal, vertical, or angled placements have no impact on the functionality of the NIR camera. Further, combinations of NIR cameras and lenses can provide opportunities to perform measurements that are currently prohibitive due to the need for a conveyor section to convey the material through a sensing array of contact electrodes or RF instruments.

The use of NIR cameras, are disclosed herein, eliminates the need for any physical contact with the wood product by any part of the moisture detection device, or even the need for the moisture detection device, i.e., the NIR camera, to be close to the wood product surface. Not only does this fact eliminate wear and tear on both the sample taking device and the wood product, but as discussed above it allows for more flexible placement of the sample taking device, i.e., the NIR camera.

In addition, unlike RF moisture detection devices and contact electrodes, NIR cameras are virtually immune to static electricity or spurious RF emissions. Consequently, use of NIR cameras as disclosed herein is far more suitable for a physical production line environment.

Finally, unlike traditional contact electrode systems that require high voltages and represent a danger to workers, NIR technology has been deemed to represent no hazards to workers or other devices by several testing and safety agencies. Consequently, the use of the disclosed NIR based moisture detection systems results in a safer and more comfortable and efficient workplace and production floor.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, or protocols. Further, the system or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic or algorithm-like descriptions and representations are the means used by those of skill in the art to most effectively and efficiently convey the substance of their work to others of skill in the art. These operations, while described functionally or logically, are understood to be implemented by computer programs or computing systems. Furthermore, it has also proven convenient at times to refer to these arrangements of operations as steps or modules or by functional names, without loss of generality.

In addition, the operations shown in the figures, or as discussed herein, are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A method for detecting moisture levels in wood products comprising:
    training one or more machine learning based moisture level detection models using Near InfraRed (NIR) image data for one or more wood products and determined corresponding moisture levels for the one or more wood products;
    providing an NIR analysis station, the NIR analysis station including one or more sources of illumination positioned to illuminate a surface of a wood product, the NIR analysis station including one or more NIR cameras positioned to capture one or more NIR images of the illuminated surface of the wood product;
    positioning a wood product to be analyzed in the NIR analysis station such that a first surface of the wood product to be analyzed is illuminated by the one or more illumination sources;
    capturing, using the one or more NIR cameras, one or more NIR images of the illuminated first surface of the wood product;
    processing the one or more NIR images of the illuminated first surface of the wood product to generate NIR image data for the illuminated first surface of the wood product;
    providing the NIR image data for the illuminated first surface of the wood product to the one or more trained machine learning based moisture level detection models;
    obtaining moisture level prediction data for the wood product from the one or more trained machine learning based moisture level detection models;
    assigning a grade to the wood product based on the moisture level prediction data for the wood product; and
    based, at least in part, on the grade assigned to the wood product, taking one or more actions with respect to the wood product.

2. The method for detecting moisture levels in wood products of claim 1 wherein the one or more trained machine learning based moisture level detection models are machine learning based model types selected from the list of machine learning based model types including:
    supervised machine learning-based models;
    semi-supervised machine learning-based models;
    unsupervised machine learning-based models;
    classification machine learning-based models;
    logistical regression machine learning-based models;
    neural network machine learning-based models; and
    deep learning machine learning-based models.

3. The method for detecting moisture levels in wood products of claim 1 wherein one or more NIR cameras are adjustably positioned to capture one or more NIR images of the illuminated surface of the wood product.

4. The method for detecting moisture levels in wood products of claim 1 wherein positioning a wood product to be analyzed in the NIR analysis station is accomplished by passing the wood product through the NIR analysis station on a conveyor system.

5. The method for detecting moisture levels in wood products of claim 1 wherein the one or more actions taken with respect to the wood product based, at least in part, on the grade assigned to the wood product, include one or more of:
    sorting the wood product into a bin or location associated with the grade assigned to the wood product;
    restricting the use of the wood product based on grade assigned to the wood product;
    rejecting the wood product based on the grade assigned to the wood product;
    sending the wood product back for further processing based on the grade assigned to the wood product;
    adjusting one or more processing parameters of a production line based on grades assigned to one or more wood products;

adjusting drying temperatures on a production line based on grades assigned to one or more wood products; and adjusting drying times on a production line based on grades assigned to one or more wood products.

6. The method for detecting moisture levels in wood products of claim 1 wherein the NIR analysis station includes one or more sources of illumination positioned to illuminate two or more surfaces of a wood product and one or more NIR cameras positioned to capture one or more NIR images of the two or more illuminated surfaces of the wood product.

7. The method for detecting moisture levels in wood products of claim 1 further comprising:

positioning a wood product to be analyzed in the NIR analysis station such that the two or more surfaces of the wood product to be analyzed are illuminated by the one or more illumination sources;

capturing, using the one or more NIR cameras, one or more NIR images of the illuminated two or more surfaces of the wood product;

processing the one or more NIR images of the illuminated two or more surfaces of the wood product to generate NIR image data for the illuminated two or more surfaces of the wood product;

providing the NIR image data for the illuminated two or more surfaces of the wood product to the one or more trained machine learning based moisture level detection models;

obtaining moisture level prediction data for the wood product from the one or more trained machine learning based moisture level detection models;

assigning a grade to the wood product based on the moisture level prediction data for the wood product; and based, at least in part, on the grade assigned to the wood product, taking one or more actions with respect to the wood product.

8. A system for detecting moisture levels in wood products comprising:

one or more trained machine learning based moisture level detection models, the one or more trained machine learning based moisture level detection models having been trained using Near InfraRed (NIR) image data for one or more wood products and corresponding determined moisture levels for the one or more wood products;

an NIR analysis station, the NIR analysis station including one or more sources of illumination positioned to illuminate a surface of a wood product, the NIR analysis station including one or more NIR cameras positioned to capture one or more NIR images of the illuminated surface of the wood product;

a wood product to be analyzed in the NIR analysis station, the wood product to be analyzed being positioned such that a first surface of the wood product to be analyzed is illuminated by the one or more illumination sources;

a physical memory, the physical memory including data representing one or more NIR images of the illuminated first surface of the wood product captured using the one or more NIR cameras;

one or more processors for processing the data representing one or more NIR images of the illuminated first surface of the wood product to generate NIR image data for the illuminated first surface of the wood product;

moisture level prediction data for the wood product obtained from the one or more trained machine learning based moisture level detection models;

a grade assignment module for assigning a grade to the wood product based on the moisture level prediction data for the wood product; and an action activation module for initializing one or more actions with respect to the wood product based, at least in part, on the grade assigned to the wood product.

9. The system for detecting moisture levels in wood products of claim 8 wherein the one or more trained machine learning based moisture level detection models are machine learning based model types selected from the list of machine learning based model types including:

supervised machine learning-based models;

semi-supervised machine learning-based models;

unsupervised machine learning-based models;

classification machine learning-based models;

logistical regression machine learning-based models;

neural network machine learning-based models; and deep learning machine learning-based models.

10. The system for detecting moisture levels in wood products of claim 8 wherein wood product to be analyzed is a veneer sheet.

11. The system for detecting moisture levels in wood products of claim 8 wherein the one or more actions taken with respect to the wood product based, at least in part, on the grade assigned to the wood product, include one or more of:

sorting the wood product into a bin or location associated with the grade assigned to the wood product;

restricting the use of the wood product based on grade assigned to the wood product;

rejecting the wood product based on the grade assigned to the wood product;

sending the wood product back for further processing based on the grade assigned to the wood product;

adjusting one or more processing parameters of a production line based on grades assigned to one or more wood products;

adjusting drying temperatures on a production line based on grades assigned to one or more wood products; and adjusting drying times on a production line based on grades assigned to one or more wood products.

12. A method for detecting moisture levels in veneer sheets comprising:

training one or more machine learning based moisture level detection models using Near InfraRed (NIR) image data for one or more veneer sheets and determined corresponding moisture levels for the one or more veneer sheets;

providing an NIR analysis station, the NIR analysis station including one or more sources of illumination positioned to illuminate a surface of a veneer sheet, the NIR analysis station including one or more NIR cameras positioned to capture one or more NIR images of the illuminated surface of the veneer sheet;

positioning a veneer sheet to be analyzed in the NIR analysis station such that a first surface of the veneer sheet to be analyzed is illuminated by the one or more illumination sources;

capturing, using the one or more NIR cameras, one or more NIR images of the illuminated first surface of the veneer sheet;

processing the one or more NIR images of the illuminated first surface of the veneer sheet to generate NIR image data for the illuminated first surface of the veneer sheet;

providing the NIR image data for the illuminated first surface of the veneer sheet to the one or more trained machine learning based moisture level detection models;

obtaining moisture level prediction data for the veneer sheet from the one or more trained machine learning based moisture level detection models;

assigning a grade to the veneer sheet based on the moisture level prediction data for the veneer sheet; and based, at least in part, on the grade assigned to the veneer sheet, taking one or more actions with respect to the veneer sheet.

13. The method for detecting moisture levels in veneer sheets of claim 12 wherein the one or more trained machine learning based moisture level detection models are machine learning based model types selected from the list of machine learning based model types including:

supervised machine learning-based models;
semi-supervised machine learning-based models;
unsupervised machine learning-based models;
classification machine learning-based models;
logistical regression machine learning-based models;
neural network machine learning-based models; and
deep learning machine learning-based models.

14. The method for detecting moisture levels in veneer sheets of claim 12 wherein one or more NIR cameras are adjustably positioned to capture one or more NIR images of the illuminated surface of the veneer sheet.

15. The method for detecting moisture levels in veneer sheets of claim 12 wherein positioning a veneer sheet to be analyzed in the NIR analysis station is accomplished by passing the veneer sheet through the NIR analysis station on a conveyor system.

16. The method for detecting moisture levels in veneer sheets of claim 12 wherein the one or more actions taken with respect to the veneer sheet based, at least in part, on the grade assigned to the veneer sheet, include one or more of:

sorting the veneer sheet into a bin or location associated with the grade assigned to the veneer sheet;
restricting the use of the veneer sheet based on grade assigned to the veneer sheet;
rejecting the veneer sheet based on the grade assigned to the veneer sheet;
sending the veneer sheet back for further processing based on the grade assigned to the veneer sheet;
adjusting one or more processing parameters of a production line based on grades assigned to one or more veneer sheets;
adjusting drying temperatures on a production line based on grades assigned to one or more veneer sheets; and
adjusting drying times on a production line based on grades assigned to one or more veneer sheets.

17. The method for detecting moisture levels in veneer sheets of claim 12 wherein the one or more sources of illumination include one or more LED light sources.

18. The method for detecting moisture levels in veneer sheets of claim 12 further comprising:

generating a greyscale to color mapping database, the greyscale to color mapping database containing data that maps one or more greyscale values to respective visible colors indicating moisture levels for one or more veneer sheets; and after processing the NIR greyscale images using the moisture level to greyscale mapping database to identify moisture levels for the first surface of the veneer sheet, processing the NIR greyscale images using the greyscale to color mapping database to generate color-based moisture level images for the first surface of the veneer sheet.

19. The method for detecting moisture levels in veneer sheets of claim 12 wherein the NIR analysis station includes one or more sources of illumination positioned to illuminate two or more surfaces of a veneer sheet and one or more NIR cameras positioned to capture one or more NIR images of the two or more illuminated surfaces of the veneer sheet.

20. The method for detecting moisture levels in veneer sheets of claim 19 further comprising:

positioning a veneer sheet to be analyzed in the NIR analysis station such that the two or more surfaces of the veneer sheet to be analyzed are illuminated by the one or more illumination sources;

capturing, using the one or more NIR cameras, one or more NIR images of the illuminated two or more surfaces of the veneer sheet;

processing the one or more NIR images of the illuminated two or more surfaces of the veneer sheet to generate NIR image data for the illuminated two or more surfaces of the veneer sheet;

providing the NIR image data for the illuminated two or more surfaces of the veneer sheet to the one or more trained machine learning based moisture level detection models;

obtaining moisture level prediction data for the veneer sheet from the one or more trained machine learning based moisture level detection models;

assigning a grade to the veneer sheet based on the moisture level prediction data for the veneer sheet; and based, at least in part, on the grade assigned to the veneer sheet, taking one or more actions with respect to the veneer sheet.

* * * * *